United States Patent
Shribak

(10) Patent No.: US 9,625,369 B2
(45) Date of Patent: Apr. 18, 2017

(54) POLYCHROMATIC POLARIZATION STATE GENERATOR AND ITS APPLICATION FOR REAL-TIME BIREFRINGENCE IMAGING

(71) Applicant: Michael Shribak, Falmouth, MA (US)

(72) Inventor: Michael Shribak, Falmouth, MA (US)

(*) Notice: Subject to any disclaimer, the term of this patent is extended or adjusted under 35 U.S.C. 154(b) by 26 days.

(21) Appl. No.: 14/807,020

(22) Filed: Jul. 23, 2015

(65) Prior Publication Data
US 2016/0103062 A1    Apr. 14, 2016

Related U.S. Application Data

(60) Provisional application No. 62/040,234, filed on Aug. 21, 2014.

(51) Int. Cl.
*G01N 21/23*     (2006.01)
*G02B 27/28*     (2006.01)
*G02B 21/00*     (2006.01)

(52) U.S. Cl.
CPC ......... *G01N 21/23* (2013.01); *G02B 21/0092* (2013.01); *G02B 27/286* (2013.01); *G01N 2201/0683* (2013.01)

(58) Field of Classification Search
CPC ... G01N 21/23; G02B 21/0068; G02B 27/286
USPC ................................. 356/365, 366
See application file for complete search history.

(56) References Cited

U.S. PATENT DOCUMENTS 7,773,299 B2 * 8/2010 Martin ............... G02B 27/0101
                                                                    296/97.1

OTHER PUBLICATIONS

Handbook of Optics, vol. 1, Chapter 28 Microscopes, Third Edition, Optical Society of America, McGraw-Hill, Inc., New York, USA, 2010.*
Shribak, Michael; Polychromatic Polarization Microscope: Bringing Colors to a Colorless World; Scientific Reports; Published Nov. 27, 2015.*

* cited by examiner

*Primary Examiner* — Roy M Punnoose

(57) ABSTRACT

Apparatus for generating polychromatic polarized light with the polarization ellipse orientation determined by the wavelength. The proposed polychromatic polarization state generator can be used in various configurations of polarized light microscope (called "polychromatic polscope") for imaging birefringent samples. The polychromatic polscope produces a spectral-modulated visual scene, in which birefringent structures are evident because their appearance is different from the background. New polarized light microscope can subtract the background and produce video-enhanced color image of birefringent structures. The obtained picture can be also mathematically processed in order to obtain a map of quantitative distribution of specimen retardation and orientation of the principal axes.

18 Claims, 21 Drawing Sheets ations. In order to increase
POLYCHROMATIC POLARIZATION STATE GENERATOR AND ITS APPLICATION FOR REAL-TIME BIREFRINGENCE IMAGING

RELATED APPLICATIONS

This application claims priority under 35 U.S.C. §119(e) to U.S. Provisional Application Ser. No. 62/040,234, entitled "Polychromatic polarization state generator/detector and its application for real-time birefringence imaging", filed on Aug. 21, 2014, which is herein incorporated by reference in its entirety.

FEDERALLY SPONSORED RESEARCH

This invention was made with Government support under NIH grant R01-EB005710. The Government may have certain rights to this invention.

BACKGROUND OF THE INVENTION

Field of Invention

This invention related to polarized light and, more particularly, to visualization and measurement of birefringent structures that possess molecular order or that are under strain.

Discussion of Related Art

Polarized light imaging of two-dimensional birefringence distribution is an established technique for analyzing the structure of various specimens. It can also be applied to study the vector or tensor fields associated with birefringence.

Polarized light has been used to obtain contrast in light microscopy. Various polarized light techniques have been developed for microscope studies of birefringence in biological unstained specimens, which caused by structural or internal anisotropy of the cell structure (S. Inoué, "A Method For Measuring Small Retardations of Structures in Living Cells", Exp. Cell Res. 2, pp. 513-517, 1951; S. Inoué and K. R. Spring, *Video Microscopy. The Fundamentals*, $2^{nd}$ ed., Plenum Press, New York, 1997; R. Oldenbourg and M. Shribak, "Microscopes", in *Handbook of Optics, Third Edition, Volume I: Geometrical and Physical Optics, Polarized Light, Components and Instruments*, (ed. M. Bass), McGraw-Hill, New York, 2010).

Common arrangements of polarized light imaging microscope include use of a pair of crossed polarizers in the beam path, with one polarizer placed prior to the sample and one after it. The sensitivity of these methods is limited, and it is difficult to detect retardance is below 5 nm.

Also the contrast of conventional polarized light images is direction sensitive. It varies proportionally with $\sin^2\alpha$, where $\alpha$ is the slow axis azimuth relatively to the direction of polarization of the illuminating light. If the specimen slow axis and the light polarization are parallel, the contrast is zero. The contrast is highest if the slow axis is oriented at 45° or 135°. It is therefore necessary to examine unknown objects at several azimuth orientations. In order to increase the contrast and remove the slow axis ambiguity we need to employ a polarization compensator introducing some ellipticity in the polarized light. In this case, the brightness is the maximal if a is 45°, and it is the minimal if $\alpha$ is 135° (N. H. Hartshorne, and A. Stuart, *Crystals and the Polarizing Microscope*, $4^{th}$ ed., Edward Arnold, London, United Kingdom, 1970).

The orientation-independent birefringence imaging has been developing by many researcher groups around the world for two decades. However, most of the currently existing techniques relay on capturing several images in time sequence or simultaneously and complex digital image processing the raw data.

The first orientation-independent techniques were reported in 1992 by Otani (Proc. SPIE 1720, 346-354 (1992)) and Noguchi (Proc. SPIE 1720, 367-378 (1992)). They employed mechanically rotated waveplates.

A polarized light microscope, which contains a mechanically rotated linear polarizer and circular analyzer, was described by Glazier and Cosier in 1997 (A. M. Glazer, and J. Cosier, "Method and Apparatus For Indicating Optical Anisotropy," UK Patent Application No. 2,310,925). Typically, six images of a specimen are taken while the linear polarizer is incremented in 30° steps; these images are then processed to yield the birefringence map, as described in an article (A. M. Glazer, J. G. Lewis, and W. Kaminsky, "An Automatic Optical Imaging System For Birefringent Media," *Proc. R. Soc. Lond. A* 452, pp. 2751-2765, 1996). The microscope is not suitable for measuring low retardance specimens because it is strongly susceptible to light intensity variations, photon statistical noise, detector read-out noise, and digitization error.

In 1994 Oldenbourg and Mei replaced rotatable waveplates with variable liquid crystal waveplates and developed a method for measurement of birefringence distribution using three consecutive elliptical and one circular polarized state of the illumination beam (U.S. Pat. No. 5,521,705). This device is known as LC-polscope. In 2000 Shribak proposed several computation algorithms, which increase sensitivity and reduce measurement time (U.S. Pat. Nos. 7,202,950, 7,239,388, 7,372,567). Currently, Perkin Elmer (Waltham, Mass.) manufactures Oosight and Abrio, which employ the LC-polscope technique and Shribak's algorithms. The price of devices is about $20 k and $40 k accordingly.

Instead of generating the raw images sequentially, Shribak et al. proposed to generate them in parallel by using a non-polarizing beamsplitter with a set of polarization analyzers in the imaging path (Proc. SPIE 4819, 56-67 (2002), U.S. Pat. No. 7,079,247). Later Kaminsky received a patent on very similar system (U.S. Pat. No. 7,522,278). The simultaneous multiple imaging technique allows to avoid artifacts caused by movement organelles in live cells. But this approach require additional custom beam multiplicator with price $15 k, large chip CCD camera with price about $15 k, and special software for image aligning.

Birefringence measuring techniques with using return-path setup were proposed by Shribak (USSR patents 1210137, 1282202, 1290090, 1290091, 1390636, 1414097, 1431484; M. I. Shribak "Autocollimating Detectors of Birefringence", in International Conference on Optical Inspection and Micromeasurements, Christophe Gorecki, Editors, Proc. SPIE 2782, pp. 805-813, 1996; and by M. I. Shribak, Y. Otani and T. Yoshizawa, "Return-Path Polarimeter For Two Dimensional Birefringence Distribution Measurement", Polarization: Measurement, Analysis, and Remote Sensing II, Dennis H., Goldstein; and David B. Chenault; Eds. Proc., SPIE 3754, pp. 144-149, 1999).

The application of two-dimensional birefringence imaging to the analysis of inner stress in construction models using photoelasticity is also well known (*Handbook on Experimental Mechanics*, Ed. by Albert S. Kobayashi, Prentice Hall: Englewood Cliffs, 1987). E. A. Patterson and co-authors offered a full-field imaging polariscope (E. A. Patterson, W. Ji, and Z. Fwang, "On Image Analysis For Birefringence Measurements in Photoelasticity", Optic Laser Engineering, 28, pp. 17-36, 1997). It has a circularly polarized illumination beam and six consecutive settings of an analyzer polarizer: left and right circular polarized settings and four linear polarized settings at 0°, 45°, 90° and 135°. The technique doesn't provide high sensitivity with low retardance specimens and use a polarization state analyzer comprising a mechanically rotated quarter waveplate and rotated linear analyzer.

While there have thus been shown various techniques for retardance measurement and two-dimensional retardance imaging, the existing techniques in the art require taking four or more readings; or are not well-suited to measurement of low-retardance samples; or do not operate with high speed; or offer less than adequate accuracy or noise.

SUMMARY OF THE INVENTION

In a first aspect, the invention features a polychromatic polarization state generator for creating a multiwavelength set of polarization states of polarized light with selected polarization ellipses. The polarization ellipses have selected ellipticity. The major axis orientation of the polarization ellipses approximately linearly depends on the wavelength.

In a second aspect, the invention features a polychromatic polarization state generator comprising of a sequence of rotatable linear polarizer, linear retarder, which phase difference approximately linearly depends on the wavelength, and achromatic quarter-wave retarder.

In a third aspect, the invention features a polychromatic polarization state generator comprising of a sequence of rotatable linear polarizer, achromatic quarter-wave retarder and polarization rotator, which polarization rotation angle approximately linearly depends on the wavelength.

In a fourth aspect, the invention features an apparatus for imaging birefringence using said polychromatic polarization state generator and achromatic circular polarizer. The sample under investigation can be imaged in transmitted or reflected light. Two configurations of the imaging birefringence apparatus could be built: (1) polychromatic polarization state generator is disposed in the illumination beam and achromatic circular polarizer is disposed in the imaging beam; (2) achromatic circular polarizer is disposed in the illumination beam and polychromatic polarization state generator is disposed in the imaging beam.

In a fifth aspect, the invention features an apparatus for imaging birefringence using two said polychromatic polarization state generators. The sample under investigation can be imaged in transmitted or reflected light. One polychromatic polarization state generator is disposed in the illumination beam and another polychromatic polarization state generator is disposed in the imaging beam.

BRIEF DESCRIPTION OF THE DRAWINGS

The invention has other advantages and features, which will be more readily apparent from the following detailed description of the invention and the appended claims, when taken in conjunction with the accompanying drawings. The drawings are not intended to be drawn to scale. In the drawings, wherein like reference characters denote similar elements throughout the various figures. In the drawing:

Figure 1B:
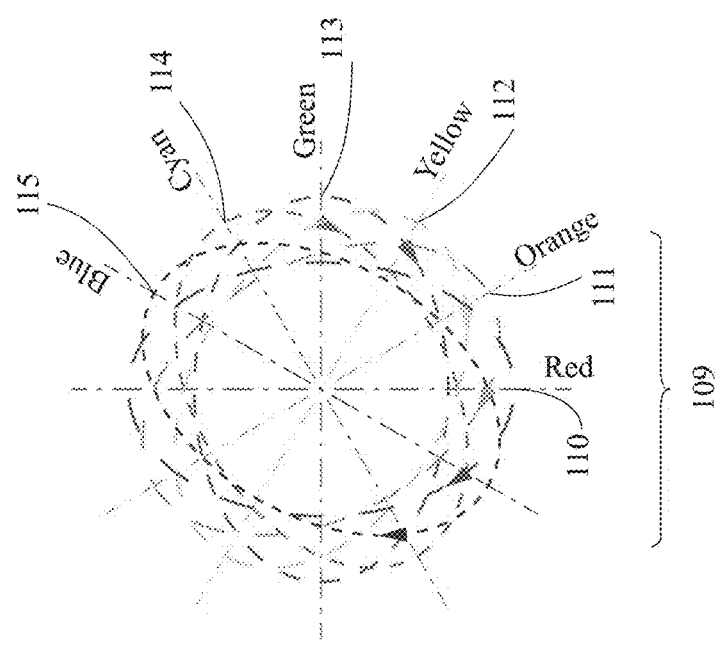
FIG. 1B is a simplified diagram of the multicolor set of output polarization ellipses produced by the first embodiment of the polychromatic polarization state generator.

The figures depict embodiments of the present invention for purposes of illustration only. One skilled in the art will readily recognize from the following discussion that alternative embodiments of the structures and methods illustrated herein may be employed without departing from the principles of the invention described herein.

DETAIL DESCRIPTION OF THE PREFERRED EMBODIMENTS

We propose new polychromatic polarization state generator, which produces polarized light with the polarization ellipse orientation determined by the wavelength. Various schematics of polychromatic polarized light microscope for imaging birefringence, called for short a "polychromatic polscope", that employs said polychromatic polarization state generator are also described. The polychromatic polscope produces a spectral-modulated visual scene, in which birefringent structures are evident because their appearance is different from the background. New microscope could also subtract the background and produces video-enhanced color image of birefringent structures. The obtained picture could be also mathematically processed in order to obtain a map of quantitative distribution of specimen retardation and orientation of the principal axes.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Figure 1A:
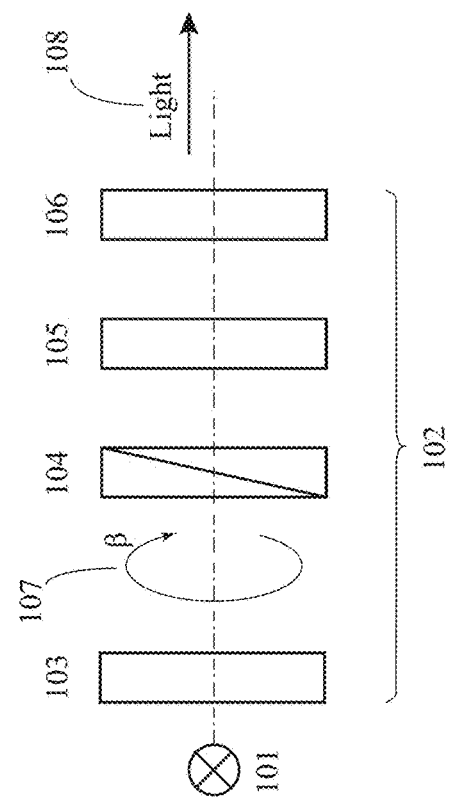
FIG. 1A is a schematic drawing of the first embodiment of polychromatic polarization state generator, which contains components for controlling ellipticity of the output polarization ellipse and producing chromatic dispersion in its major axis orientation.

An example of optical configuration of the first embodiment of the polychromatic polarization state generator with a broadband light source is shown in FIG. 1A. The system consists of light source 101, polychromatic polarization state generator 102, which includes bandpass filter 103, linear polarizer 104, linear retarder 105 at azimuth 45° and achromatic quarter-wave retarder 106 at azimuth 0°. The linear polarizer can be oriented at angle β, as it is shown by arrow 107. The setup could also use a fixed polarizer and adjust angle β with rotatable achromatic half-wave retarder. The light beam propagation direction is shown by arrow 108.

The spectrum of the beam, which is radiated by the light source, is shaped by the filter 103. The filter 103 can be placed in any location in the light beam path. Instead of the broadband light source one can use several monochromatic light sources, for example lasers. In this case the bandpass filter is not needed. The filter 103 is also not required if the spectrum of the beam is effectively restricted by the detector spectral sensitivity. For example, radiation spectrum of the Sun or an incandescent bulb is effectively restricted by human eye sensitivity from about 400 nm to about 700 nm.

Any type of retarder, which introduces approximately 90°-phase shift between orthogonal polarization components for all used wavelengths, can work as the achromatic quarter-wave retarder 106. For example, achromatic 90°-phase shift can be created by a combination of two or three retarders of materials having different birefringence dispersion to minimize deviation from quarter-wave retardance across a broad wavelength range (J. M. Beckers, "Achromatic linear retarders," *Appl. Opt.* 10, 973-975 (1971); P. Hariharan, "Broad-band apochromatic retarder: choice of materials," *Opt. Laser Technol.* 34, 509-511 (2002)). Pancharatnam achromatic retarders (S. Pancharatnam, "Achromatic combinations of birefringent plates. Part I. An achromatic circular polarizer," *Proc. Indian Acad. Sci. A*, 41, 130-136 (1955); S. Pancharatnam, "Achromatic combinations of birefringent plates. Part II. An achromatic quarter-wave plate," *Proc. Indian Acad. Sci. A*, 41, 137-144 (1955)) that use multiple plates of a single material with different fast axis orientations are also suitable. The almost perfect achromatic 90°-phase shift can be achieved by using the Fresnel rhomb, Mooney rhomb or other reflective rhomb-type quarter-wave retarders (F. Mooney, "A Modification of the Fresnel Rhomb," *J. Opt. Soc. Am.* 42, 181-181 (1952); J. M. Bennett, "A Critical Evaluation of Rhomb-Type Quarterwave Retarders," *Appl. Opt.* 9, 2123-2129 (1970)).

Linear retarder 105 and achromatic quarter-wave retarder 106 form a polarization converter, which transforms the incoming linear polarized multispectral beam into elliptically polarized beams, which polarization ellipse orientation depends on the wavelength.

Let us describe the polarization transformation more detail. The polarizer 104 produces linear polarized beam with selected orientation β. The linear retarder 105 introduces phase difference α between orthogonal X- and Y-polarization components. The phase difference δ depends on wavelength λ in the following way (N. H. Hartshorne, and A. Stuart, *Crystals and the Polarizing Microscope*, 4$^{th}$ ed., Edward Arnold, London, United Kingdom, 1970):

$$\delta(\lambda) = \frac{360°}{\lambda}(n_e - n_o)t, \quad (1)$$

where t is thickness of the linear retarder 105 and $n_e$ and $n_o$ are extraordinary and ordinary refractive indices, respectively.

Then the beam passes through the achromatic quarter-wave retarder 106. The major axis orientation ψ of the output polarization ellipse and its ellipticity angle ε can be found from the following equations (M. Shribak, "Complete polarization state generator with one variable retarder and its application for fast and sensitive measuring of two-dimensional birefringence distribution," *J. Opt. Soc. Am. A* 28, 410-419 (2011)):

$$\begin{cases} \varepsilon = \beta \\ \psi = \delta(\lambda)/2 \end{cases}, \text{if } \beta \neq -45° \text{ or } 45°. \quad (2)$$

In the case $\beta=-45°$ or $\beta=45°$ the output beam has left or right circular polarization, respectively, and orientation of the polarization ellipse major axis is not defined.

Thus, the proposed polychromatic polarization generator can produce any polarization state of the output beam, which ellipticity $\varepsilon$ is one-to-one function of the polarizer angle $\beta$ and major axis orientation $\psi$ is one-to-one function of the phase shift a that depends on wavelength $\lambda$:

$$\begin{cases} -45° \leq \varepsilon \leq 45°, \text{if } -45° \leq \beta \leq 45° \\ 0° \leq \psi \leq 180°, \text{if } 0° \leq \delta(\lambda) \leq 360° \end{cases} \quad (3)$$

Let's select a continuous spectral domain with the shortest wavelength $\lambda_{min}$ and the longest wavelength $\lambda_{max}$. In many cases the spectral dispersion of birefringence is low and we can approximately assume that extraordinary and ordinary refractive indices $n_e$ and $n_o$ do not depend on the wavelength. According to equation (1) the minimal phase difference $\delta_{min}$ corresponds to the longest wavelength $\lambda_{max}$ and the maximum phase difference $\delta_{max}$ occurs at the shortest wavelength $\lambda_{min}$:

$$\begin{cases} \delta_{min} = \frac{360°}{\lambda_{max}}(n_e - n_o)t \\ \delta_{max} = \frac{360°}{\lambda_{min}}(n_e - n_o)t \end{cases} \quad (4)$$

Dependence of the major axis orientation of the polarization ellipses $\psi$ on the wavelength $\lambda$ is a one-to-one function in the selected spectral domain if $\delta_{max}-\delta_{min}=360°$. Then, using the above equation, we could find thickness t of the linear retarder 105, which satisfy this condition:

$$t = \frac{\lambda_{max} \cdot \lambda_{min}}{(\lambda_{max} - \lambda_{min})(n_e - n_o)}. \quad (5)$$

We can also write the corresponding expression for retardance:

$$\text{retardance} = t(n_e - n_o) = \frac{\lambda_{max} \cdot \lambda_{min}}{(\lambda_{max} - \lambda_{min})}. \quad (6)$$

For example, the visible spectrum from 440 nm to 660 nm would require linear retarder with retardance about 1320 nm.

After substituting (5) and (1) into the $2^{nd}$ equations (2) we can find the spectral dependence of the major axis orientation $\psi(\lambda)$:

$$\psi(\lambda) = 180° \frac{1}{\lambda} \frac{\lambda_{max} \cdot \lambda_{min}}{(\lambda_{max} - \lambda_{min})}. \quad (7)$$

The corresponding minimal and maximal values of orientation angles $\psi_{min}$ and $\psi_{max}$, which occur at the maximal and minimal wavelengths $\lambda_{max}$ and $\lambda_{min}$, are the following:

$$\begin{cases} \psi_{min} = 180° \frac{\lambda_{min}}{(\lambda_{max} - \lambda_{min})} \\ \psi_{max} = 180° \frac{\lambda_{max}}{(\lambda_{max} - \lambda_{min})} \end{cases} \quad (8)$$

As one could see to see the difference between the minimal and maximal orientation angles $\psi_{min}$ and $\psi_{max}$, equals to 180°.

The equation (7) could be rewritten in the following way:

$$\psi(\lambda) = \psi_{min} + 180° \frac{\lambda_{min}}{(\lambda_{max} - \lambda_{min})} \left( \frac{\lambda_{max}}{\lambda} - 1 \right). \quad (9)$$

Let's choose an orientation of the major axis of polarization ellipse with the maximum wavelength $\lambda_{max}$ as the initial direction. Then in new coordinate system $\psi_{min}=0°$ and formula (9) can be simplified:

$$\psi(\lambda) = 180° \frac{\lambda_{min}}{(\lambda_{max} - \lambda_{min})} \left( \frac{\lambda_{max}}{\lambda} - 1 \right). \quad (10)$$

In particular, for visible spectrum from 440 nm to 660 nm we get the next equation:

$$\psi(\lambda) = 360° \left( \frac{660}{\lambda} - 1 \right), \quad (11)$$

where wavelength $\lambda$ is in nanometers. As one can see if $\lambda=660$ nm then $\psi=0°$, and if $\lambda=440$ nm then $\psi=180°$.

Using the above formula the inverse dependence of wavelength $\lambda$ on the selected orientation of the polarization ellipse $\psi$:

$$\lambda = \frac{360°}{\psi + 360°} 660, \quad (12)$$

where orientation of the polarization ellipse $\psi$ is in degrees and wavelength $\lambda$ is in nanometers.

An example of the angular distribution of polarization ellipses 109 for visible spectrum from 440 nm to 660 nm is shown in FIG. 1B. The major axis of red polarization ellipse 110 ($\lambda=660$ nm) is oriented along the initial axis ($\psi=0°$). Then the major axes of orange polarization ellipse 111 ($\lambda=609$ nm), yellow polarization ellipse 112 ($\lambda=566$ nm), green polarization ellipse 113 ($\lambda=528$ nm), cyan polarization ellipse 114 ($\lambda=495$ nm) and blue polarization ellipse 115 ($\lambda=466$ nm) are oriented at 30°, 60°, 90°, 120° and 150° to the initial axis, correspondently. All polarization ellipses have the same ellipticity $\varepsilon$, which is equal to orientation angle $\beta$ of the linear polarizer 104. For instance, if $\beta=0°$ then all spectral components became linearly polarized with vibration planes parallel to the major axes. In another extreme case when $\beta=-45°$ or $\beta=45°$, the output beam becomes left or right circularly polarized for all wavelengths and orientation of the polarization ellipse major axis is not defined.

In similar way one can perform analysis of the first embodiment of the polychromatic polarization state generator for another spectral domain and/or take into account dispersion of birefringence of the linear retarder.

Figure 2B:
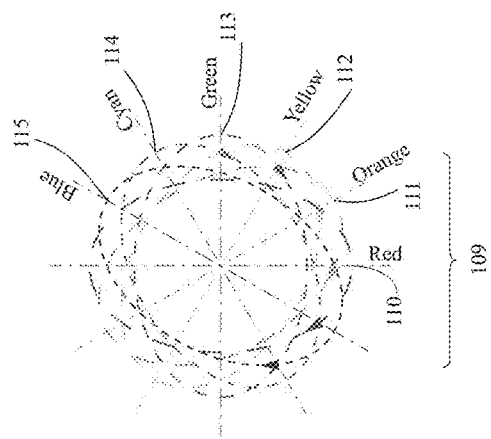
FIG. 2B is a simplified diagram of the multicolor set of output polarization ellipses produced by the second embodiment of polychromatic polarization state generator.
Figure 2A:
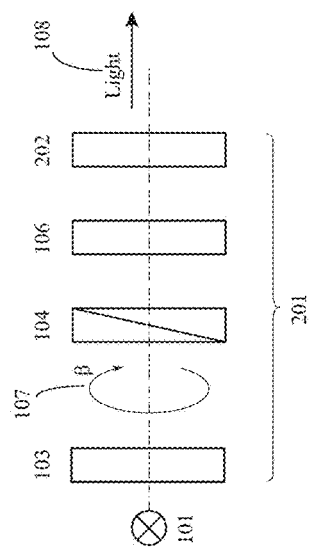
FIG. 2A is a schematic drawing of the second embodiment of polychromatic polarization state generator, which contains components for controlling ellipticity of the output polarization ellipse and producing chromatic dispersion in its major axis orientation.

An example of optical configuration of the second embodiment of the polychromatic polarization state generator with a broadband light source is shown in FIG. 2A. The system consists of light source 101, polychromatic polarization state generator 201, which includes bandpass filter 103, linear polarizer 104, achromatic quarter-wave retarder 106 at azimuth 0° and polarization rotator 202. The linear polarizer can be oriented at angle β, as it is shown by arrow 107. The setup could also use a fixed polarizer and adjust angle β with rotatable achromatic half-wave retarder. The light beam propagation direction is shown by arrow 108. The filter 103 can be placed in any location in the light beam path. Achromatic quarter-wave retarder 106 and polarization rotator 202 form a polarization converter, which transforms the incoming linear polarized multispectral beam into elliptically polarized beams, which polarization ellipse orientation depends on the wavelength.

Any type of polarization rotator, which manifests a spectral dispersion of optical activity, can be employed in the polychromatic polarization state generator. One can use a plane parallel plate made of an optically active anisotropic crystal, which is cut perpendicular to the optic axis (so called z-cut). If polarized light travels along the crystal optic axis its polarization ellipse rotates. For most other directions of propagation, the effect of optical rotation and linear birefringence are superposed, that of the latter being general predominant and the polarization ellipse becomes distorted. The best known example of this type of crystals is α-quartz.

In optically active cubic crystals the rotation effect is the same for all directions of propagation. Similar directional independent rotation of the polarization ellipse also has been noted in many liquids and in solution of optically active crystals. For example, measurement of polarization rotation is widely employed for determining concentration of sugar in solution by saccharimeters.

In all well-authenticated cases of optical activity, the crystal or molecular structure is of the type which can exist in two enantiomorphous forms, i.e. forms which are related to one another as an object and its mirror image, but do not differ in any other way. In one form the spirals for a given direction are right-handed and in the other left-handed, and their specific rotations are the same numerically but have opposite sign. In crystals, the amount of rotation of light for a specific wavelength for a one millimeter thickness of a plate is the specific rotation, and is either right-handed (dextrorotatory) or left-handed (levorotatory) as viewed looking toward the light source. For liquids it is common practice to measure the specific rotation in a column 10 cm in length. Lists of minerals and inorganic and organic compounds that are known to be optically active have been tabulated in many places (N. H. Hartshorne, and A. Stuart, *Crystals and the Polarizing Microscope*, 4$^{th}$ ed., Edward Arnold, London, United Kingdom, 1970; E. E. Wahlstrom, *Optical Crystallography*, 5$^{th}$ ed., Wiley, New York, 1979).

Let us describe the polarization transformation the second embodiment of the polychromatic polarization state generator more detail. The polarizer 104 produces linear polarized beam with selected orientation β. After achromatic quarter-wave retarder 106 the beam becomes elliptically polarized with ellipticity angle ε and major axis orientation ψ (M. Shribak, "Polarization". In: *Handbook of Optical Metrology: Principles and Applications* (ed. T. Yoshizawa), CRC Press, Boca Raton, Fla., USA, pp. 339-350 (2009)):

$$\begin{cases} \varepsilon = \beta \\ \psi = 0° \end{cases} \quad (13)$$

Then the elliptically polarized beam passes through the polarization rotator 202, which rotates the polarization ellipse by angle φ without changing the ellipticity (E. Hecht, *Optics*, 4$^{th}$ ed., Addison-Wesley, 2001):

$$\phi(\lambda) = \frac{180°}{\lambda}(n_L - n_R)t, \quad (14)$$

where t is thickness of the polarization rotator 202, $n_L$ and $n_R$ are refractive indices of the left and right circular polarizations, respectively. If $n_L > n_R$ then the polarization rotator is d-rotatory, and if $n_R > n_L$ then the polarization rotator is l-rotatory.

Then the major axis orientation ψ of polarization ellipse and its ellipticity angle ε of output beam 108 are following:

$$\begin{cases} \varepsilon = \beta \\ \psi = \phi(\lambda) \end{cases} \quad (15)$$

In the selected spectral domain the minimal and maximal polarization rotations $\phi_{min}$ and $\phi_{max}$ correspond to at the longest and shortest wavelengths $\lambda_{max}$ and $\lambda_{min}$, respectively:

$$\begin{cases} \phi_{min} = \frac{180°}{\lambda_{max}}(n_L - n_R)t \\ \phi_{max} = \frac{180°}{\lambda_{min}}(n_L - n_R)t \end{cases} \quad (16)$$

Dependence of the major axis orientation of the polarization ellipses ψ on the wavelength λ is a one-to-one function in the selected spectral domain if $\phi_{max} - \phi_{min} = 180°$. In many cases the spectral dispersion of circular birefringence $n_L - n_R$ is low and we can approximately assume that it does not depend on the wavelength. Then we could find thickness t of the polarization rotator 202, which satisfy this condition:

$$t = \frac{\lambda_{max} \cdot \lambda_{min}}{(\lambda_{max} - \lambda_{min})(n_L - n_R)}. \quad (17)$$

We can also write the corresponding expression for circular retardance:

$$\text{circular retardance} = t(n_L - n_R) = \frac{\lambda_{max} \cdot \lambda_{min}}{(\lambda_{max} - \lambda_{min})}. \quad (18)$$

For example, the visible spectrum from 440 nm to 660 nm would require polarization rotator with circular retardance about 1320 nm.

After substituting (18) and (14) into the 2$^{nd}$ equations (15) we can find the spectral dependence of the major axis orientation ψ(λ):

$$\psi(\lambda) = 180° \frac{1}{\lambda} \frac{\lambda_{max} \cdot \lambda_{min}}{(\lambda_{max} - \lambda_{min})}. \quad (19)$$

The corresponding minimal and maximal values of orientation angles $\psi_{min}$ and $\psi_{max}$, which occur at the maximal and minimal wavelengths $\lambda_{max}$ and $\lambda_{min}$, are the following:

$$\begin{cases} \psi_{min} = 180° \frac{\lambda_{min}}{(\lambda_{max} - \lambda_{min})} \\ \psi_{max} = 180° \frac{\lambda_{max}}{(\lambda_{max} - \lambda_{min})} \end{cases}. \quad (20)$$

As one could see to see the difference between the minimal and maximal orientation angles $\psi_{min}$ and $\psi_{max}$, equals to 180°.

The equation (19) could be rewritten in the following way:

$$\psi(\lambda) = \psi_{min} + 180° \frac{\lambda_{min}}{(\lambda_{max} - \lambda_{min})} \left( \frac{\lambda_{max}}{\lambda} - 1 \right). \quad (20)$$

Let's choose an orientation of the major axis of polarization ellipse with the maximum wavelength $\lambda_{max}$ as the initial direction. Then in new coordinate system $\psi_{min}=0°$ and formula (9) can be simplified:

$$\psi(\lambda) = 180° \frac{\lambda_{min}}{(\lambda_{max} - \lambda_{min})} \left( \frac{\lambda_{max}}{\lambda} - 1 \right). \quad (21)$$

In particular, for visible spectrum from 440 nm to 660 nm we get the next equation:

$$\psi(\lambda) = 360° \left( \frac{660}{\lambda} - 1 \right), \quad (22)$$

where wavelength $\lambda$ is in nanometers. As one can see if $\lambda=660$ nm then $\psi=0°$, and if $\lambda=440$ nm then $\psi=180°$.

Using the above formula the inverse dependence of wavelength $\lambda$ on the selected orientation of the polarization ellipse $\psi$:

$$\lambda = \frac{360°}{\psi + 360°} 660, \quad (23)$$

where orientation of the polarization ellipse $\psi$ is in degrees and wavelength $\lambda$ is in nanometers.

An example of the angular distribution of polarization ellipses 109 for visible spectrum from 440 nm to 660 nm is shown in FIG. 2B. The major axis of red polarization ellipse 110 ($\lambda=660$ nm) is oriented along the initial axis ($\psi=0°$). Then the major axes of orange polarization ellipse 111 ($\lambda=609$ nm), yellow polarization ellipse 112 ($\lambda=566$ nm), green polarization ellipse 113 ($\lambda=528$ nm), cyan polarization ellipse 114 ($\lambda=495$ nm) and blue polarization ellipse 115 ($\lambda=466$ nm) are oriented at 30°, 60°, 90°, 120° and 150° to the initial axis, correspondently. All polarization ellipses have the same ellipticity E, which is equal to orientation angle $\beta$ of the linear polarizer 104. For instance, if $\beta=0°$ then all spectral components became linearly polarized with vibration planes parallel to the major axes. In another extreme case when $\beta=-45°$ or $\beta=45°$, the output beam becomes left or right circularly polarized for all wavelengths and orientation of the polarization ellipse major axis is not defined.

In similar way one can perform analysis of the second embodiment of the polychromatic polarization state generator for another spectral domain and/or take into account dispersion of circular birefringence of the polarization rotator.

Figure 3:
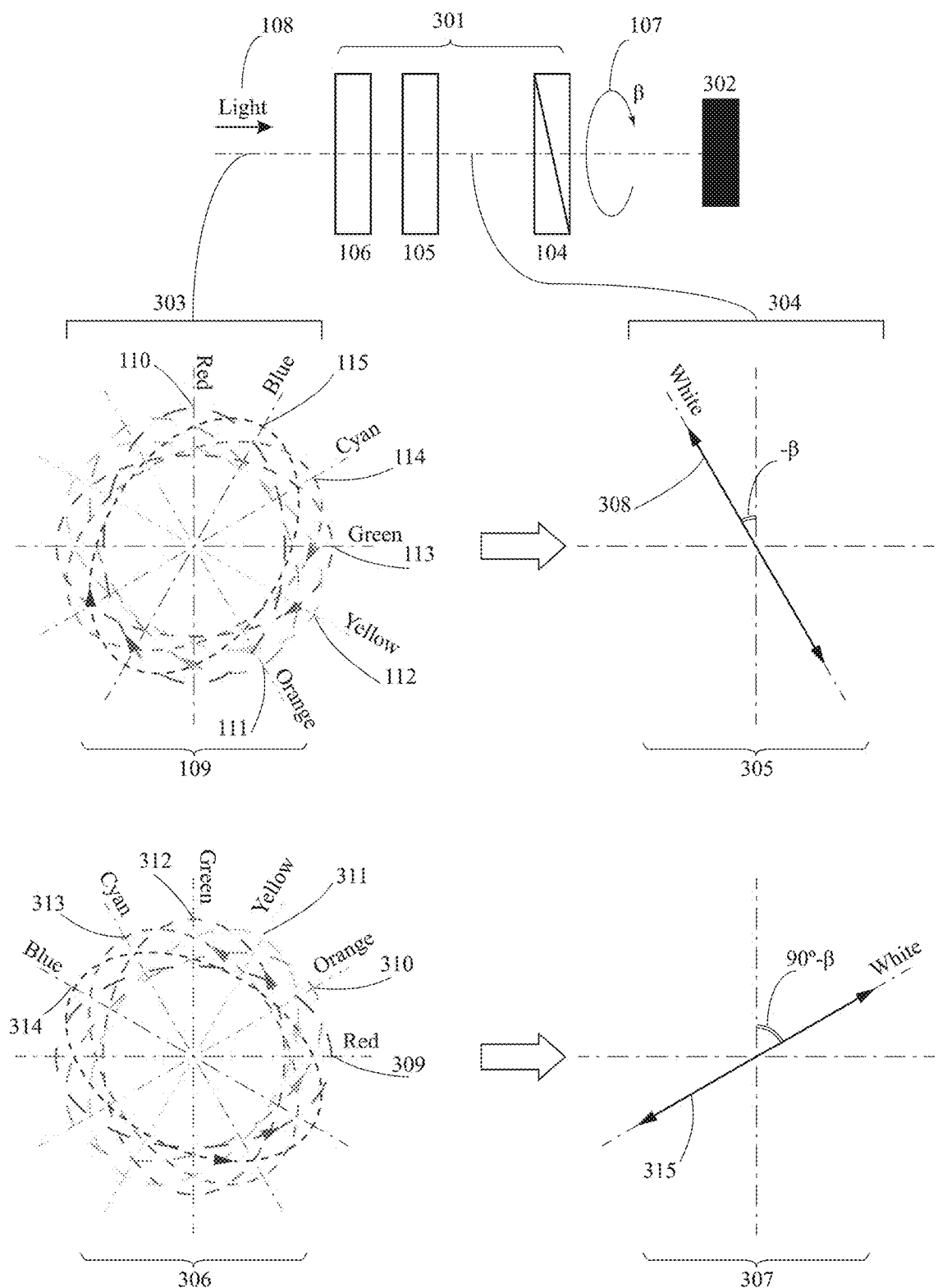
FIG. 3 is a schematic of the first embodiment of the polychromatic polarization state generator, which operates as a polarization state detector, and diagrams showing polarization transformation of the beam.

Taking into account the principle of reciprocity in polarization optics (see, for example, R. J. Potton, "Reciprocity in optics," Reports on Progress in Physics 67, 717-754 (2004)) we can show that the proposed polarization state generator in the inverted orientation works as a polarization state detector. FIG. 3 illustrates schematic of the first embodiment of the polychromatic polarization state generator, which operates as a polarization state detector, and provides an explanation of polarization transformation of the incoming beam.

The polychromatic polarization state detector 301 includes achromatic quarter-wave retarder 106, linear retarder 105 and rotatable linear polarizer 104. Light detector 302, for example a color CCD camera, determines spectral intensity distribution in the output beam. This is exactly same schematic, which is depicted in FIG. 1A, except a light source 101 has been replaced with the light detector 302. We also omitted bandpass filter 103 for simplicity. Because the device is turned over by 180° the orientation angles of its components become inverse. So, the linear polarizer 104 will be oriented at angle $-\beta$. The beam propagation direction is shown by arrow 108.

Polarization diagrams in FIG. 3 illustrate transformations of polarization states during propagation through the optical system. The left column 303 shows two sets of polarization ellipses at the entrance of polarization state detector, before achromatic quarter-wave retarder 106. The right column 304 displays two polarization states after propagation of the beam through polarization converter, created by achromatic quarter-wave retarder 106 and linear retarder 105.

At first, let's consider input polarization state 109 that is the same as created by polarization state generator shown in FIG. 1A and FIG. 1B. During the inverse propagation the polarization stats will be reproduced back and all spectral components after the linear retarder 105 (see diagram 305) will have linear polarization 308 oriented at angle $-\beta$. Then the polarizer 107 will transmit all light toward detector 302.

Next, let's consider another input polarization state 306, which is orthogonal to polarization state shown in diagram 109. Each polarization spectral ellipse 309 (red), 310 (orange), 311 (yellow), 312 (green), 313 (cyan) and 314 (blue) is orthogonal to the corresponding polarization ellipses 110 (red), 111 (orange), 112 (yellow), 113 (green), 114 (cyan) and 115 (blue) in diagram 109. That means their major axes are perpendicular and their ellipticity values are the same numerically but have opposite sign. Then the polarization converter, consisting of the achromatic quarter-wave retarder 106 and linear retarder 105, will transform all income spectral components into linear polarization state 315 (see diagram 307). Linear polarization 315 oriented at angle 90°−$\beta$. Then the polarizer 107 will block all light.

The second embodiment of the polychromatic polarization state generator in the inverse orientation can also operate as a polarization state detector. However, in order to compensate spectral distribution of polarization ellipse orientation, which is created by optically active polarization rotator 202 (see FIG. 2A), the corresponding polarization state detector has to employ polarization rotator with opposite handedness.

Figure 4:
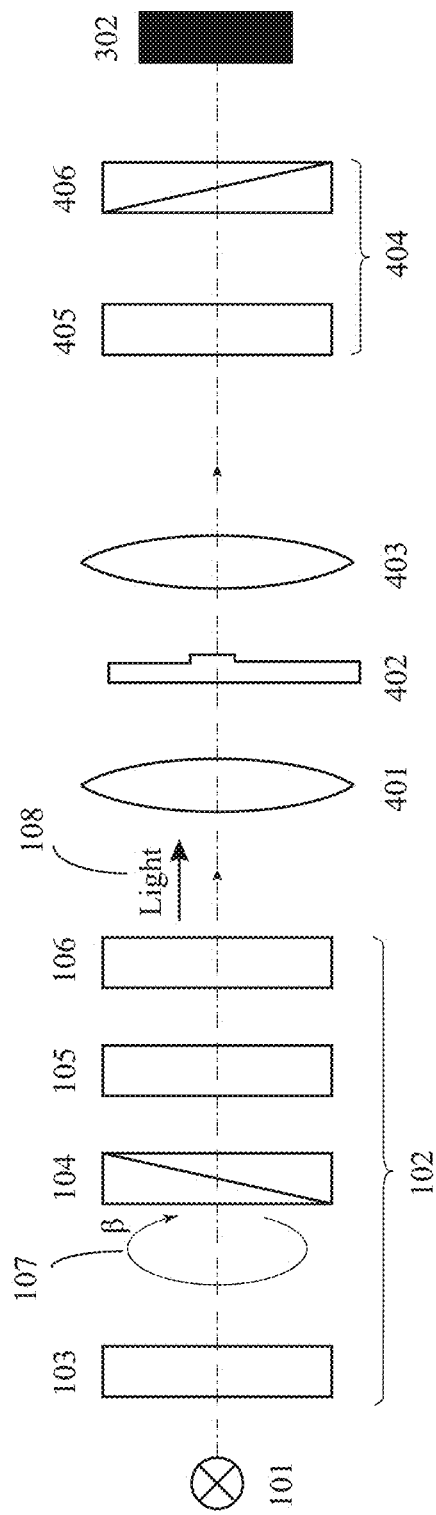
FIG. 4 is a schematic drawing of transmitting apparatus for imaging birefringence (polychromatic polscope) with the first embodiment of the polychromatic polarization state generator in the illumination path and achromatic circular polarizer in the imaging path.

FIG. 4 shows a schematic drawing of a transmitting polychromatic polarized light microscope (or polychromatic polscope for short) with the first embodiment of polychromatic polarization state generator in the illumination path and an achromatic circular analyzer in the imaging path. The polychromatic polscope consists of a light source 101, polychromatic polarization state generator 102, condenser lens 401, birefringent specimen under investigation 402, objective lens 403, achromatic circular analyzer 404, and color CCD camera 302. The polychromatic polarization state generator 102 includes bandpass filter 103, linear polarizer 104, linear retarder 105 at azimuth 45° and achromatic quarter-wave retarder 106 at azimuth 0°. The linear polarizer can be oriented at angle β, as it is shown by arrow 107. The light beam propagation direction is shown by arrow 108. The achromatic circular analyzer 404 could be formed by achromatic quarter waveplate 405 with orientation 45° and linear polarizer 406 with orientation 0°.

Let's assume that the illumination beam 108 has polarization distribution shown in FIG. 1B and the slow axis of the birefringent specimen under investigation 402 is oriented at 60°. Hence, the specimen's slow axis is parallel to the major axis of the cyan polarization ellipse 114 and perpendicular to the major axis of the orange ellipse 111. In this case, ellipticity of the cyan component would be enhanced and ellipticity of the orange component would be reduced. The specimen appears in cyan color. If the specimen is turned by 90°, then specimen's retardance reduces ellipticity of the cyan ellipse 114 and increases ellipticity of the orange polarization ellipse 111. The specimen appears in orange color. Angle β is chosen to obtain the best image contrast. The empty background area does not affect the beam ellipticity. Therefore the achromatic circular analyzer transmits all wavelengths equally. The background is uniformly grey while birefringent particles are colorized in accordance with orientation. The image brightness reflects amount of retardation, and the image color depicts the slow azimuth orientation. The image is registered by a color CCD camera 302.

In polychromatic polscope the hue is determined by orientation of the birefringent structure, not by its retardance. Thus, full spectrum color can be achieved at a much lower retardance than in a case of a regular polarization microscope. The polychromatic polscope generates the orientation-independent birefringence image without requiring any digital computation. An eye can directly see the colored striking and visually appealing images in real time. The previously colorless organelles, cells, and tissues birefringent images become vividly colored.

Figure 5:
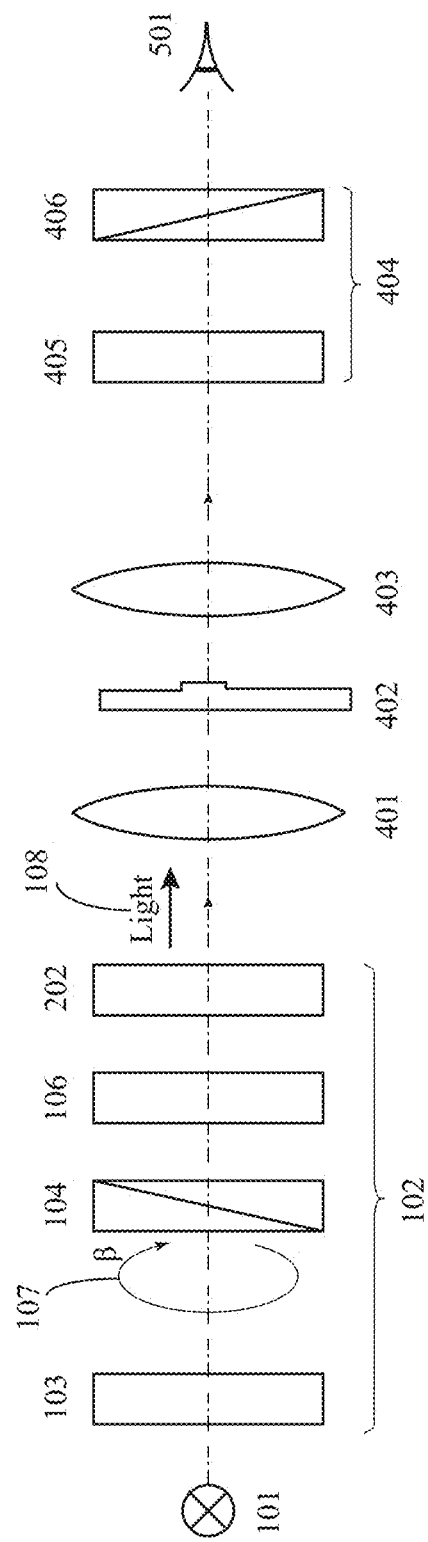
FIG. 5 is a schematic drawing of transmitting polychromatic polscope for visual observation of birefringence with the second embodiment of the polychromatic polarization state generator in the illumination path and achromatic polarizer analyzer in the imaging path.

FIG. 5 shows a schematic drawing of a polychromatic polscope for the visual observation of birefringent specimens. This microscope setup consists of a light source 101, polychromatic polarization state generator 102, condenser lens 401, birefringent specimen under investigation 402, objective lens 403 and achromatic circular analyzer 404. The polychromatic polarization state generator 102 includes bandpass filter 103, linear polarizer 104, linear retarder 105 and achromatic quarter-wave retarder 106. The linear polarizer can be oriented at angle β, as it is shown by arrow 107. The light beam propagation direction is shown by arrow 108. The achromatic circular analyzer 404 could be formed by achromatic quarter waveplate 405 and linear polarizer 406. This setup is a modification of polscope that is depicted in FIG. 4, where an eye 501 replaces the color CCD camera 302.

Figure 6:
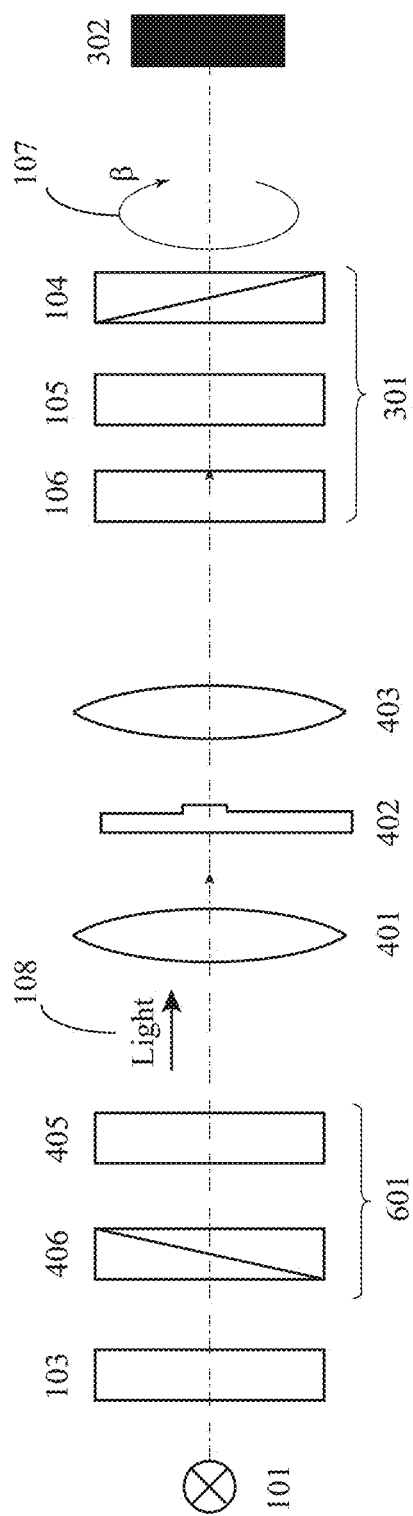
FIG. 6 is a schematic drawing of transmitting polychromatic polscope with achromatic circular polarizer in the illumination path and the first embodiment of polychromatic polarization state generator in the imaging path.

FIG. 6 shows transmitting polychromatic polscope with achromatic circular polarizer in the illumination path and the first embodiment of polychromatic polarization state generator in the imaging path. The polychromatic polarization state generator works as a polarization state detector (see FIG. 3). This polscope setup consists of a light source 101, bandpass filter 103, achromatic circular polarizer 601, condenser lens 401, birefringent specimen under investigation 402, objective lens 403, polychromatic polarization state detector 301 and color CCD camera 302. Polarizer 406 with orientation 0° and achromatic quarter waveplate 405 with orientation 45° form the achromatic circular polarizer 601. The polychromatic polarization state detector 301 includes achromatic quarter-wave retarder 106, linear retarder 105 and linear polarizer 104. The linear polarizer 104 can be oriented at angle β, as it is illustrated by arrow 107. The light beam propagation direction is depicted by arrow 108. Polychromatic polscope shown in FIG. 6 is installed in inverse direction in comparison to the schematic in FIG. 4. Taking into account the principle of reciprocity in polarization optics we can show that the both schematics work in the same way and provide the same images.

Figure 7:
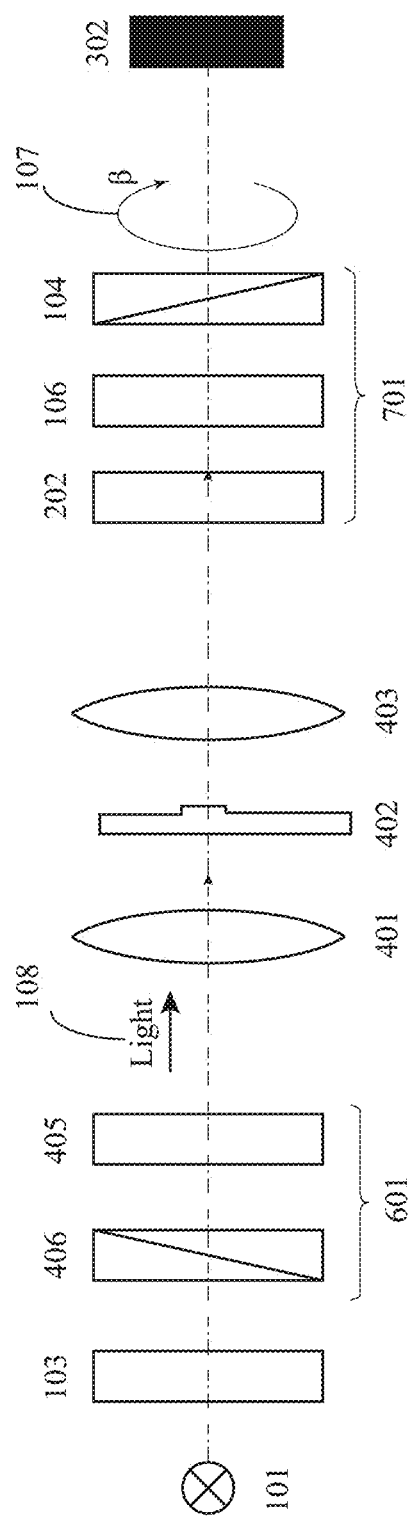
FIG. 7 is a schematic drawing of transmitting polychromatic polscope with achromatic circular polarizer in the illumination path and the second embodiment of polychromatic polarization state generator in the imaging path.

FIG. 7 shows transmitting polychromatic polscope with achromatic circular polarizer in the illumination path and the second embodiment of polychromatic polarization state generator in the imaging path. Here the polychromatic polarization state generator serves as a polarization state detector (see FIG. 3). The schematic consists of a light source 101, bandpass filter 103, achromatic circular polarizer 601, condenser lens 401, birefringent specimen under investigation 402, objective lens 403, polychromatic polarization state detector 701 and color CCD camera 302. Polarizer 406 with orientation 0° and achromatic quarter waveplate 405 with orientation 45° form the achromatic circular analyzer 601. The polychromatic polarization state detector 701 includes polarization rotator 202, achromatic quarter-wave retarder 106 and linear polarizer 104. The linear polarizer 104 can be oriented at angle β, as it is illustrated by arrow 107. The light beam propagation direction is depicted by arrow 108. Polychromatic polscope, which is shown in FIG. 7, functions is the same way as polscope depicted in FIG. 6.

Figure 8:
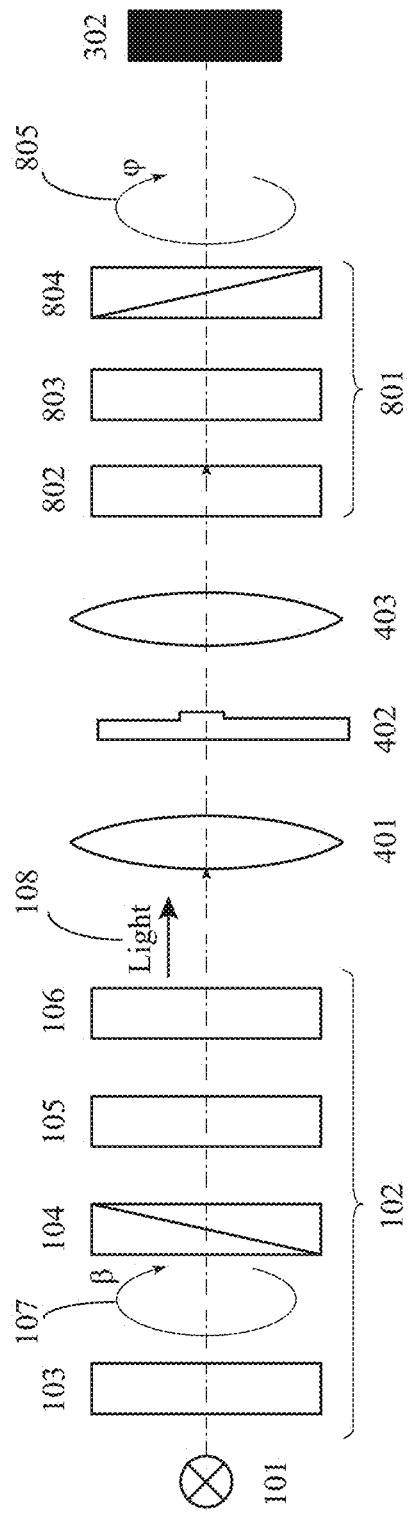
FIG. 8 is a schematic drawing of transmitting polychromatic polscope with two first embodiments of polychromatic polarization state generators.

FIG. 8 shows transmitting polychromatic polscope with two first embodiments of polychromatic polarization state generators 102 and 801. Here the polychromatic polarization state generator 102 is located in the illumination path, while the polarization state generator 801 is placed in inverse orientation in the imaging path. Thus, the polychromatic polarization state generator 801 functions as a polarization state detector (see FIG. 3). The shown polychromatic polscope also includes a light source 101, bandpass filter 103, condenser lens 401, birefringent specimen under investigation 402, objective lens 403 and color CCD camera 302. Polychromatic polarization state generator 102 consists of linear polarizer 104, linear retarder 105 and achromatic quarter-wave retarder 106. The linear polarizer can be oriented at angle β, as it is shown by arrow 107. The light beam propagation direction is depicted by arrow 108. Polychromatic polarization state detector 801 includes achromatic quarter-wave retarder 802, linear retarder 803 and linear polarizer 804. The linear polarizer 804 can be oriented at angle φ, as it is illustrated by arrow 805.

Design of polychromatic polscope, which is shown in FIG. 8, is versatile. If the linear polarizer 804 is oriented at angle φ=±45° then the polarization state detector 801 transmits polarized light with ellipticity $\epsilon=\pm 45°$ (see formula (2)) and blocks light with ellipticity $\epsilon=\mp 45°$, correspondently. Thus, if $\phi=\pm 45°$ then the polarization state detector 801 works as right or left achromatic circular polarizer. This is configuration of polychromatic polscope with first embodiments of polychromatic polarization state generator in the illumination path and achromatic circular polarizer in the imaging path, which is described in FIG. 4.

If the linear polarizer 104 is oriented at angle $\beta=\pm 45°$ then the polarization state generator 102 transmits circularly polarized light with ellipticity $\epsilon=\pm 45°$ (see formula (2)). Thus, if $\beta=\pm 45°$ then the polarization state generator 102 works as right or left achromatic circular polarizer. This is configuration of polychromatic polscope with achromatic circular polarizer in the illumination path and first embodiments of polychromatic polarization state generator in the imaging path, which is described in FIG. 6.

If linear polarizer 104 is oriented at angle $\beta=\pm 45°$ and linear polarizer 804 is oriented at angle $\phi=\pm 45°$ then the both polarization state generator 102 and polarization state detector 801 work as achromatic circular polarizers. But a specimen with low retardation does not exhibit any colors between crossed circular polarizers and it shows a weak grey contrast only. In order to see the colors we have to compensate some spectral polarization components by changing the beam ellipticity. Therefore one of the generators should produce the elliptically polarized light in order to obtain the interference colors. However the combination of achromatic elliptical and circular polarizers creates the grey background in the image non-birefringent area. So, a color birefringent structure always appears with grey non-birefringent background in polychromatic polscope configuration using an achromatic circular polarizer (see FIG. 4, FIG. 5, FIG. 6, FIG. 7).

Polychromatic polscope, which is shown in FIG. 8, allows to receive a color image of birefringent structure with black non-birefringent background. If linear polarizer 104 is oriented at angle $\beta=0°$ and linear polarizer 804 is oriented at angle $\phi=0°$ then polarization state generator 102 and polarization state detector 801 transmit polarized light with ellipticity $\epsilon=0°$ (see formula (2)). Thus, if $\beta=0°$ and $\phi=0°$ then polarization state generator 102 and polarization state detector 801 work as linear polarizers with principal axis orientation depending on wavelength. If the principal axes are crossed then a non-birefringent specimen does not change beam polarization and the light is blocked. Let's place a birefringent specimen. If polarization is parallel to a principal plane of the specimen the beam polarization does not change. The corresponding spectral band is blocked by the polarization state detector 801. If polarization is oriented at $\pm 45°$ to principal plane of the specimen then we observe the maximal change of polarization. Thus, the birefringent structure becomes color with black non-birefringent background. Therefore polychromatic polscope, which is shown in FIG. 8, allows to achieve significantly higher image contrast.

Figure 9:
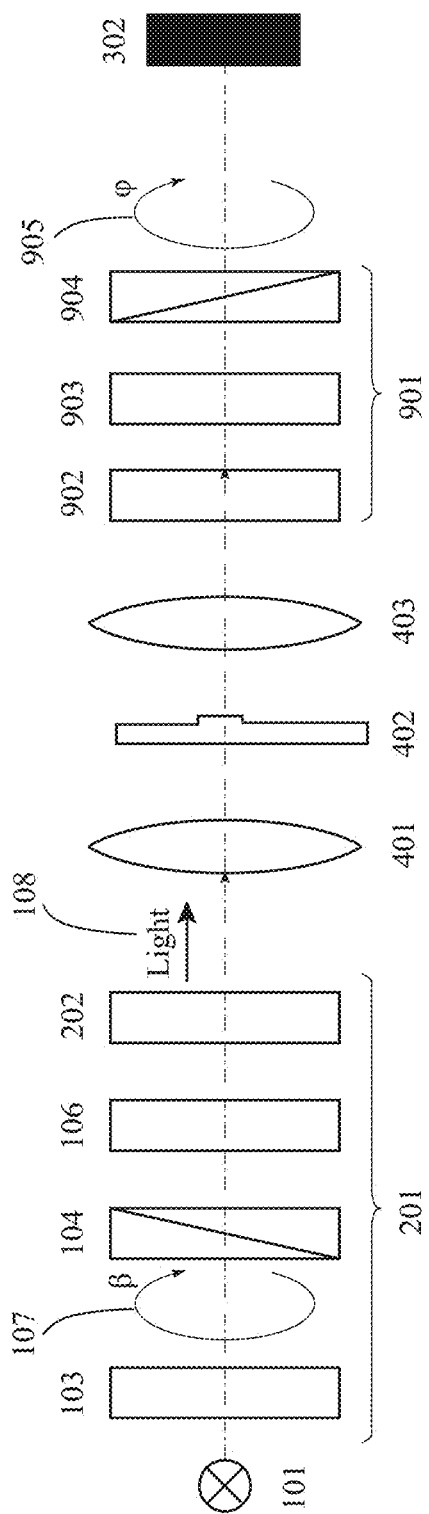
FIG. 9 is a schematic drawing of transmitting polychromatic polscope with two second embodiments of polychromatic polarization state generators in the illumination and imaging paths.

FIG. 9 shows transmitting polychromatic polscope with two second embodiments of polychromatic polarization state generators 201 and 901. The polychromatic polarization state generator 201 is located in the illumination path, and the polarization state generator 901 is placed in the inverse orientation in the imaging path. The polychromatic polarization state generator 901 is used as a polarization state detector. The shown polychromatic polscope also includes a light source 101, bandpass filter 103, condenser lens 401, birefringent specimen under investigation 402, objective lens 403 and color CCD camera 302. Polychromatic polarization state generator 201 consists of linear polarizer 104, achromatic quarter-wave retarder 106 and polarization rotator 202. The linear polarizer can be oriented at angle $\beta$, as it is shown by arrow 107. The light beam propagation direction is depicted by arrow 108. Polychromatic polarization state detector 901 includes polarization rotator 902, achromatic quarter-wave retarder 903 and linear polarizer 904. The linear polarizer 904 can be oriented at angle $\phi$, as it is illustrated by arrow 905. Polychromatic polscope, which is shown in FIG. 9, functions is the same way as polscope depicted in FIG. 8.

Figure 10:
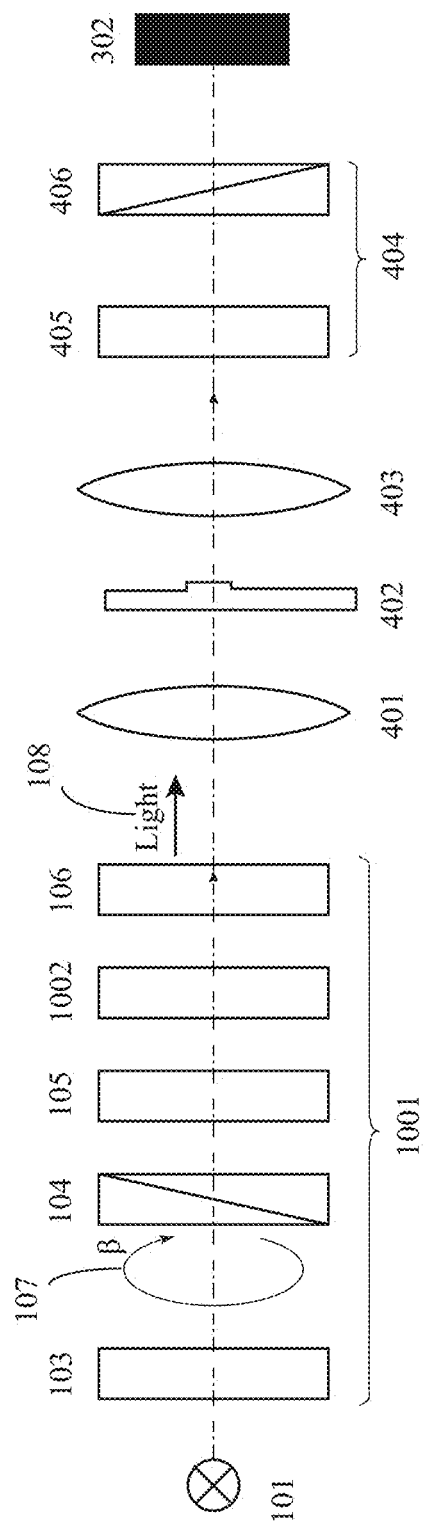
FIG. 10 is a schematic drawing of transmitting polychromatic polscope with the first embodiment of polychromatic polarization state generator containing additional variable retarder in the illumination path and an achromatic circular polarizer in the imaging path.

FIG. 10 shows a schematic drawing of transmitting polychromatic polscope with the first embodiment of polychromatic polarization state generator containing additional variable retarder in the illumination path and an achromatic circular polarizer in the imaging path. This schematic allows to study colored specimens, for instance with H&E staining, and achieve more sensitive detection of the birefringence. The polychromatic polscope consists of a light source 101, polychromatic polarization state generator 1001, condenser lens 401, birefringent specimen under investigation 402, objective lens 403, achromatic circular analyzer 404 and color CCD camera 302. The polychromatic polarization state generator 1001 includes bandpass filter 103, linear polarizer 104, linear retarder 105 at azimuth 45°, additional variable linear retarder 1002 at azimuth 45°, and achromatic quarter-wave retarder 106 at azimuth 0°. The linear polarizer can be oriented at angle $\beta$, as it is shown by arrow 107. The light beam propagation direction is shown by arrow 108. The achromatic circular analyzer 404 could be formed by achromatic quarter waveplate 405 with orientation 45° and linear polarizer 406 with orientation 0°. In principle, variable linear retarder 1002 can be placed with between linear polarizer 104 and linear retarder 105.

A standard untwisted nematic liquid crystal cell, Freedericksz cell, which works in the Electrically Controlled Birefringence (ECB) mode, can be employed as variable retarder 1002. The Freedericksz cell configuration is different from the twisted nematic configuration typically used in liquid crystal displays. Conventional Freedericksz ECB cell consists of homogeneously parallel aligned liquid crystal directors. The ECB mode uses the applied voltage to change the tilt of the liquid crystal molecules, as a result, the birefringence is changed as a function of the tilt angle. When no voltage is applied, the liquid crystal molecule's directors are aligned parallel to the cell substrates and the retardance it at a maximum. When a voltage is applied, an electric field is introduced which supplies a torque to the liquid crystal molecules; the retardance is decreased. The molecules near the substrates are not able to fully rotate, and so the retardance does not quite get to zero. Conventional ECB cell has retardance range from 0.1 to two wave ($2\lambda$) at 700 nm.

It is also possible to use an ECB cell with vertical alignment (VA ECB) as variable retarder 1002. The liquid crystal molecule's directors are aligned perpendicular (vertical) to the cell substrates if no voltage is applied, and the retardance is at a minimum (zero). Applied voltage turns the liquid crystal directors, and so the retardance is increased. The vertically aligned LC cell exhibits the highest contrast value among all LC cells. Another its merit is fast response speed due to thin cell gap. It does not require a compensation film in order to get zero retardance. The VA ECB has some shortcomings, such as lower retardance range from 0 to half wave ($\lambda/2$) at 700 nm, and reduced contrast for off axis rays.

It is also possible to manufacture a regular ECB cell or with vertically alignment ECB cell, which have thicker liquid crystal layer with retardance about 1320 nm. In this case the thick cell would function as the variable retarder 1002 and linear retarder 105 at the same time.

Changing retardation by the variable retarder 1002 would rotate major axis of spectral polarization ellipses of the illumination beam. So, colors of the birefringent particles would be changing accordingly. However, the non-birefringent background would stay constant. Then the birefringent structures become clear visible because of their different appearance when modulated against the background.

The polychromatic polscope configuration, depicted in FIG. 10, can be used for visual observation of birefringence structures in the specimen under investigation, with naked eye, in the real-time. A setup for visual observation with liquid crystal variable retarder 1002 can employ a simple signal generator of a square wave with frequency 1-10 kHz and sweeping amplitude within a range 2-4 volts. The voltage range of the generator has to provide the phase variation δ within 360° (see formula (2)), which corresponds to changing the ellipse azimuth ψ by 180°. It is also possible to utilize a "blinking mode", when the variable retarder 1002 generates several polarization states in alternation, which produces a blinking view at the microscope eyepieces. Turning the polarizer can maximize the image contrast. It is convenient to use a cycle frequency about 4 Hz for the best observation.

It is also possible to captured two images with complimentary colors where the set of polarization ellipses are turned by 90°. Image subtraction would enhance modulated color areas and remove gray background and colors produces by staining or/and specimen spectral absorption.

Figure 11:
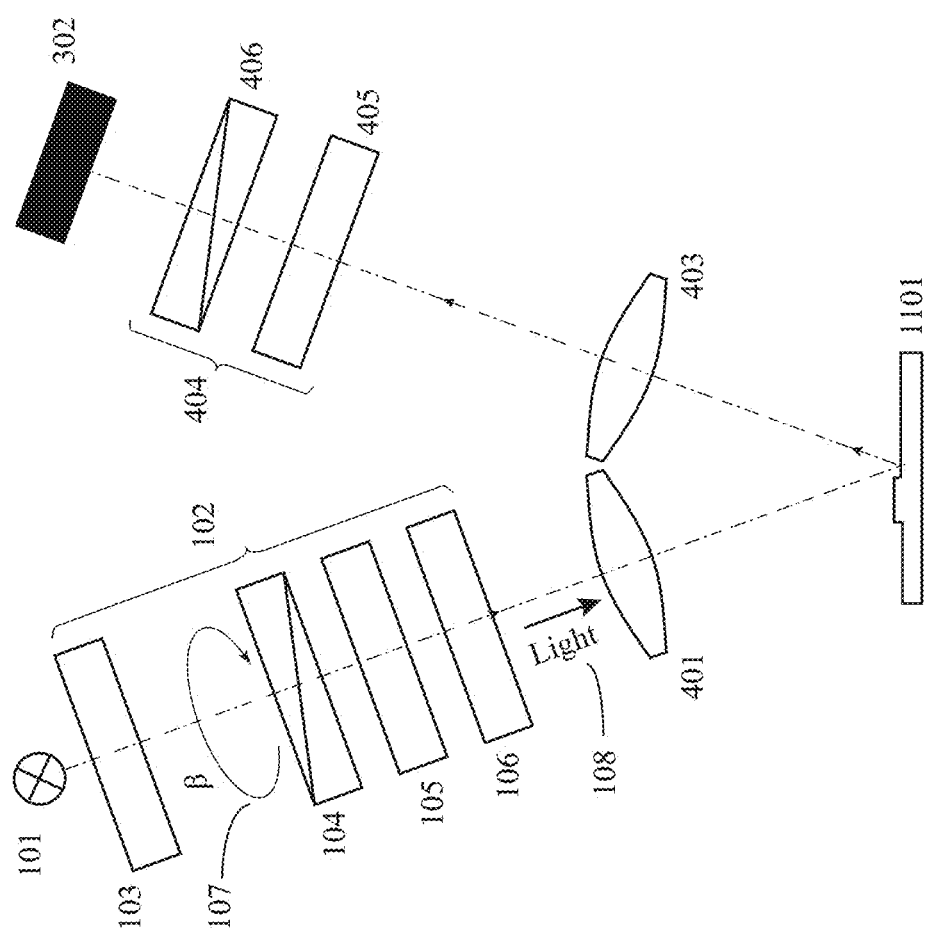
FIG. 11 is a schematic drawing of reflected polychromatic polscope with the first embodiment of polychromatic polarization state generator in the illumination path and achromatic circular polarizer in the imaging path.

FIG. 11 shows a schematic of reflected polychromatic polscope with the first embodiment of polychromatic polarization state generator in the illumination path and achromatic circular polarizer in the imaging path. The polychromatic polscope consists of a light source 101, polychromatic polarization state generator 102, condenser lens 401, reflecting birefringent specimen under investigation 1101, objective lens 403, achromatic circular analyzer 404 and color CCD camera 302. The polychromatic polarization state generator 102 includes bandpass filter 103, linear polarizer 104, linear retarder 105 at azimuth 45° and achromatic quarter-wave retarder 106 at azimuth 0°. The linear polarizer can be oriented at angle β, as it is shown by arrow 107. The light beam propagation direction is shown by arrow 108. The achromatic circular analyzer 404 could be formed by achromatic quarter waveplate 405 with orientation 45° and linear polarizer 406 with orientation 0°. Reflected polychromatic polscope, which is shown in FIG. 11, functions is the same way as transmitted polscope depicted in FIG. 4, except the beam in reflected by the specimen instead of transmitted. The shown reflected polscope schematic can also employ the second embodiment of polychromatic polarization state generator 201 (see FIG. 2A) in the illumination path.

Figure 12:
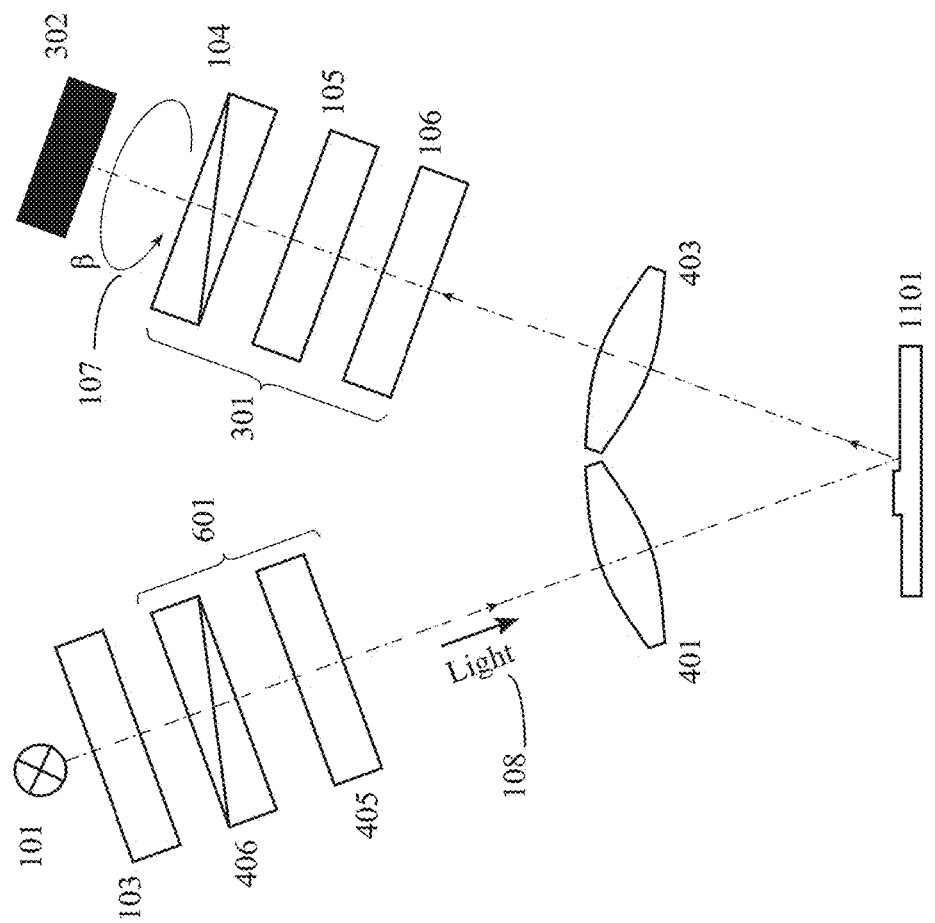
FIG. 12 is a schematic drawing of reflected polychromatic polscope with achromatic circular polarizer in the illumination path and the first embodiment of polychromatic polarization state generator in the imaging path.

FIG. 12 shows a schematic of reflected polychromatic polscope with achromatic circular polarizer in the illumination path and the first embodiment of polychromatic polarization state generator in the imaging path. The polychromatic polarization state generator serves as a polarization state detector (see FIG. 3). The polscope setup consists of a light source 101, bandpass filter 103, achromatic circular polarizer 601, condenser lens 401, reflecting birefringent specimen under investigation 1101, objective lens 403, polychromatic polarization state detector 301 and color CCD camera 302. Polarizer 406 with orientation 0° and achromatic quarter waveplate 405 with orientation 45° form the achromatic circular analyzer 601. The polychromatic polarization state detector 301 includes achromatic quarter-wave retarder 106, linear retarder 105 and linear polarizer 104. The linear polarizer 104 can be oriented at angle β, as it is illustrated by arrow 107. The light beam propagation direction is depicted by arrow 108. Reflected polychromatic polscope, which is shown in FIG. 12, functions is the same way as transmitted polscope depicted in FIG. 6, except the beam in reflected by the specimen instead of transmitted. The shown reflected polscope schematic can also employ the second embodiment of polychromatic polarization state generator 201 (see FIG. 2A) in the illumination path.

Figure 13:
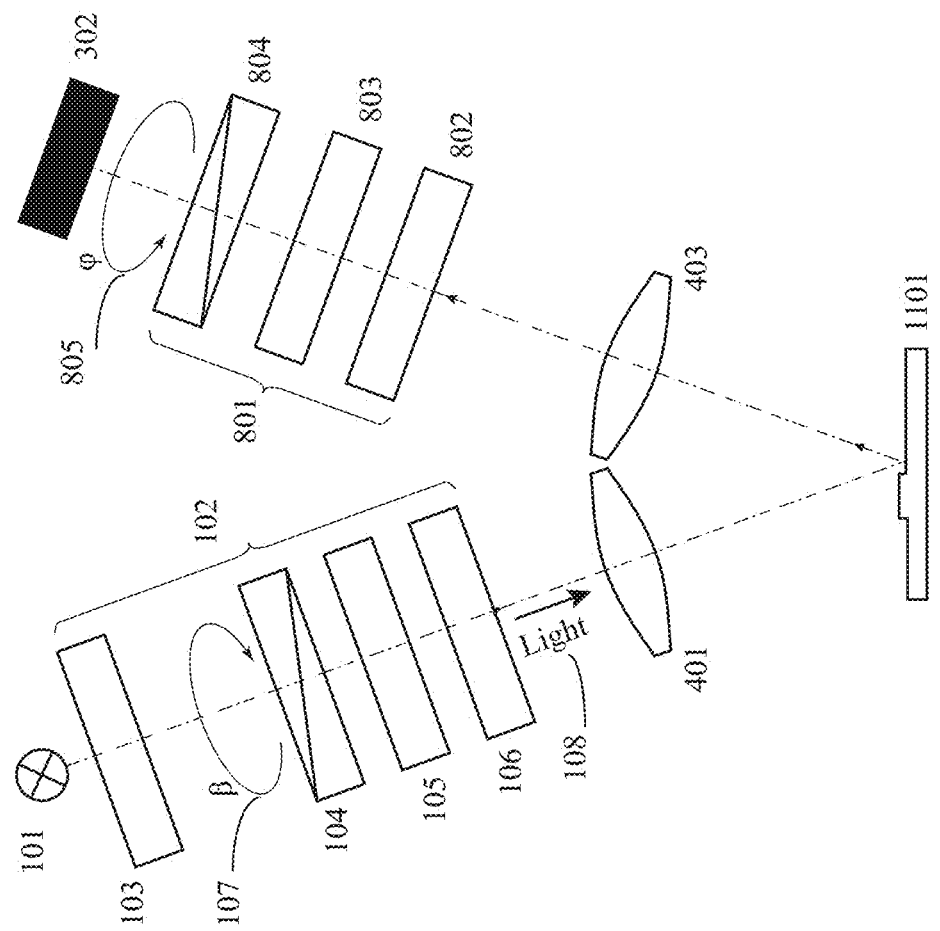
FIG. 13 is a schematic drawing of reflected polychromatic polscope with two first embodiments of polychromatic polarization state generator.

FIG. 13 shows a schematic of reflected polychromatic polscope with two first embodiments of polychromatic polarization state generator, 102 and 801. The generator 102 controls polarization states of the illumination beam. The polychromatic polarization state generator 801 is oriented backward in the imaging path. Here the generator 801 serves as a polarization state detector. The shown polychromatic polscope also includes a light source 101, bandpass filter 103, condenser lens 401, reflecting birefringent specimen under investigation 1101, objective lens 403 and color CCD camera 302. Polychromatic polarization state generator 102 consists of linear polarizer 104, linear retarder 105 and achromatic quarter-wave retarder 106. The linear polarizer can be oriented at angle β, as it is shown by arrow 107. The light beam propagation direction is depicted by arrow 108. Polychromatic polarization state detector 801 includes achromatic quarter-wave retarder 802, linear retarder 803 and linear polarizer 804. The linear polarizer 804 can be oriented at angle ϕ, as it is illustrated by arrow 805. Reflected polychromatic polscope, which is shown in FIG. 13, functions is the same way as transmitted polscope depicted in FIG. 8, except the beam in reflected by the specimen instead of transmitted. The shown reflected polscope schematic can also employ the second embodiment of polychromatic polarization state generator 201 (see FIG. 2A) in the illumination path.

Figure 14:
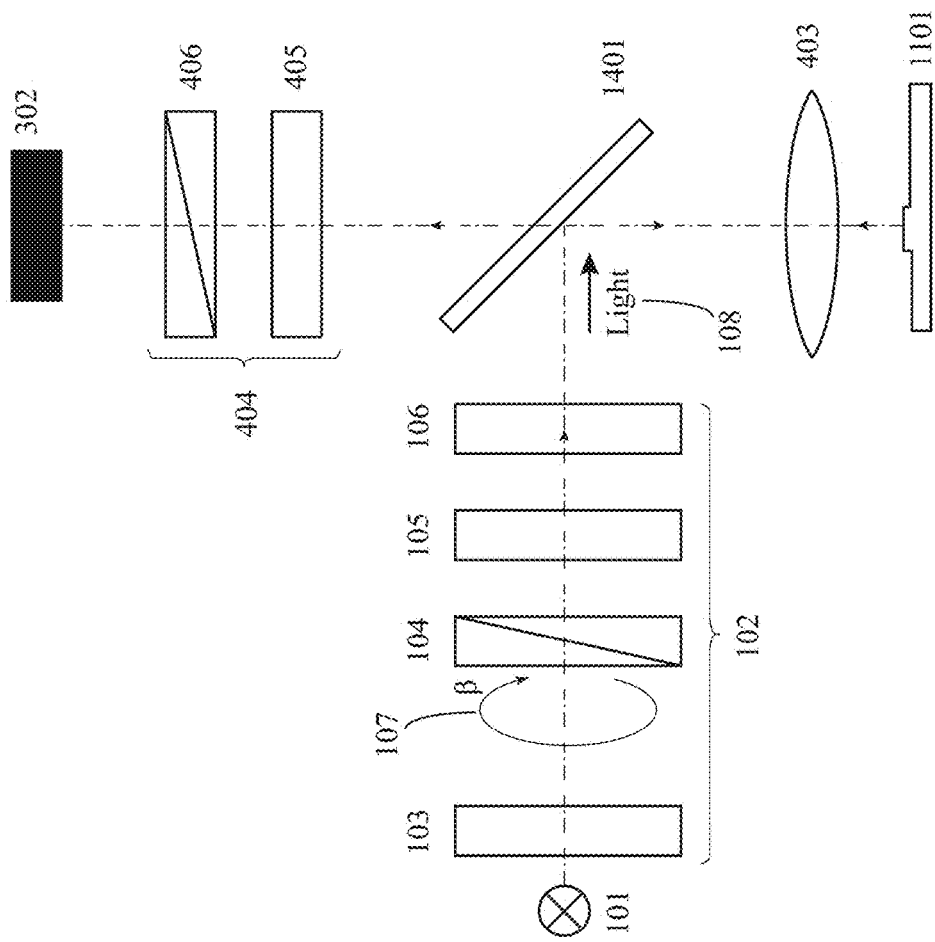
FIG. 14 is a schematic drawing of reflected polychromatic polscope with the first embodiment of polychromatic polarization state generator in the illumination path, achromatic circular polarizer in the imaging path and a non-polarizing beamsplitter.

FIG. 14 shows a schematic of reflected polychromatic polscope with the first embodiment of polychromatic polarization state generator in the illumination path, achromatic circular polarizer in the imaging path and a non-polarizing beamsplitter. The depicted polscope consists of a light source 101, polychromatic polarization state generator 102, non-polarizing beamsplitter 1401, objective lens 403, reflecting birefringent specimen under investigation 1101, achromatic circular analyzer 404 and color CCD camera 302. The polychromatic polarization state generator 102 includes bandpass filter 103, linear polarizer 104, linear retarder 105 at azimuth 45° and achromatic quarter-wave retarder 106 at azimuth 0°. The linear polarizer can be oriented at angle β, as it is shown by arrow 107. The light beam propagation direction is shown by arrow 108. The achromatic circular analyzer 404 could be formed by achromatic quarter waveplate 405 with orientation 45° and linear polarizer 406 with orientation 0°. Reflected polychromatic polscope, which is shown in FIG. 14, functions is the same way as transmitted polscope depicted in FIG. 4, except the beam in reflected by the specimen instead of transmitted and objective lens 403 is used twice, for illuminating the specimen and for imaging. The shown reflected polscope schematic can also employ the second embodiment of polychromatic polarization state generator 201 (see FIG. 2A) in the illumination path.

Figure 15:
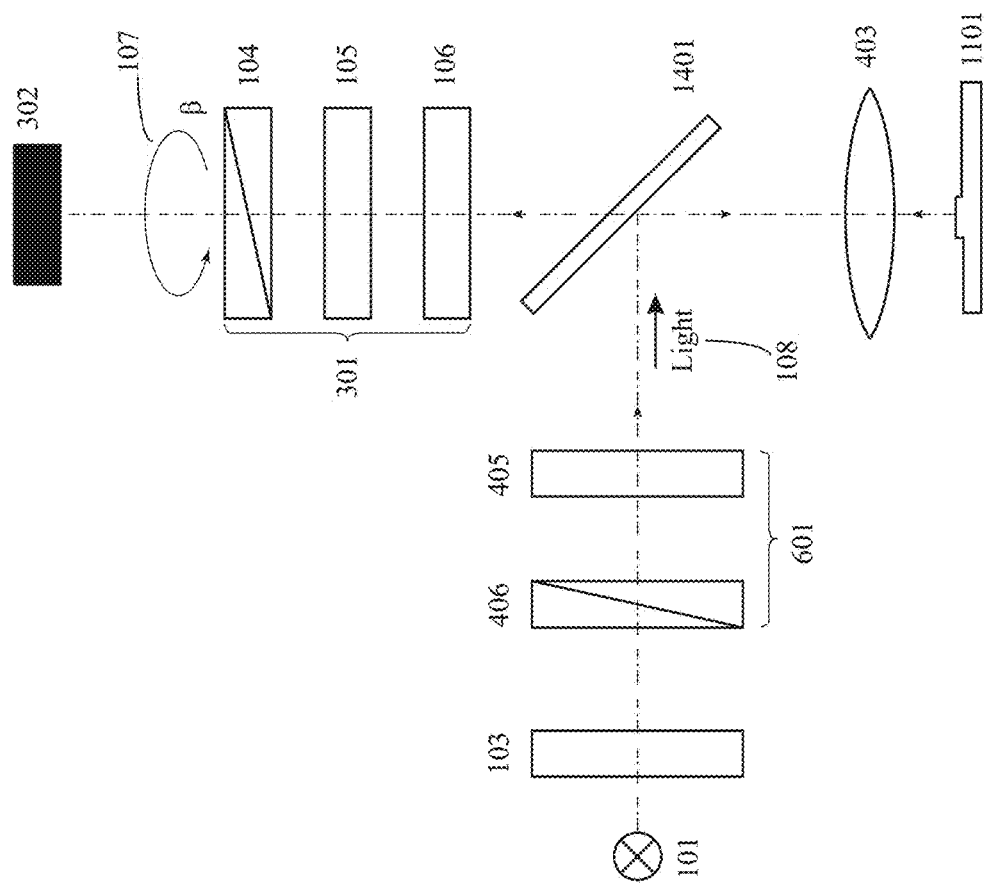
FIG. 15 is a schematic drawing of reflected polychromatic polscope with achromatic circular polarizer in the illumination path and the first embodiment of polychromatic polarization state generator in the imaging path and non-polarizing beamsplitter.

FIG. 15 shows a schematic of reflected polychromatic polscope with achromatic circular polarizer in the illumination path, non-polarizing beamsplitter, and first embodiment of polychromatic polarization state generator in the imaging path. The depicted apparatus consists of light source 101, bandpass filter 103, achromatic circular analyzer 601, non-polarizing beamsplitter 1401, objective lens 403, reflecting birefringent specimen under investigation 1101, polychromatic polarization state detector 301 and color CCD camera 302. Polarizer 406 with orientation 0° and achromatic quarter waveplate 405 with orientation 45° form the achromatic circular polarizer 601. The polychromatic polarization state detector 301 includes achromatic quarter-wave retarder 106 at azimuth 0°, linear retarder 105 at azimuth 45°, and linear polarizer 104. The linear polarizer 104 can be oriented at angle β, as it is illustrated by arrow 107. The light beam propagation direction is depicted by arrow 108. Reflected polychromatic polscope, which is shown in FIG. 15, functions is the same way as transmitted polscope depicted in FIG. 6, except the beam in reflected by the specimen instead of transmitted and objective lens 403 is used twice, for illuminating the specimen and for imaging. The shown reflected polscope schematic can also employ the second embodiment of polychromatic polarization state generator 201 (see FIG. 2A) instead of first embodiment of polychromatic polarization state detector 301.

Figure 16:
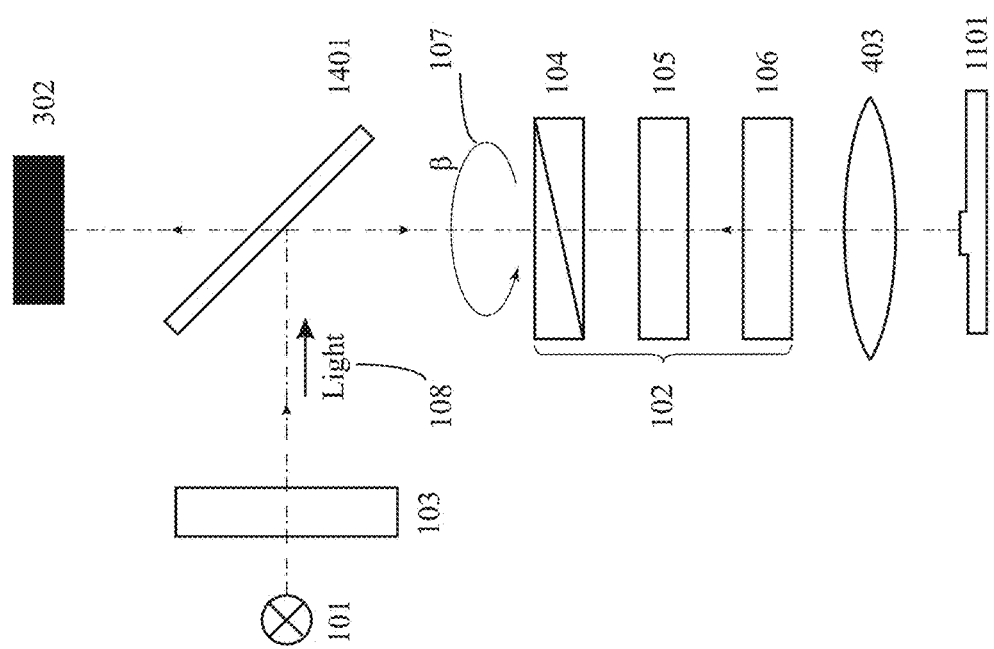
FIG. 16 is a schematic drawing of reflected polychromatic polscope with the first embodiment of polychromatic polarization state generator in the common path and non-polarizing beamsplitter.

FIG. 16 shows a schematic of reflected polychromatic polscope with non-polarizing beamsplitter and first embodiment of polychromatic polarization state generator in the common beam path. The shown setup consists of light source 101, bandpass filter 103, non-polarizing beamsplitter 1401, polychromatic polarization state generator 102, objective lens 403, reflecting birefringent specimen under investigation 1101, and color CCD camera 302. The polychromatic polarization state generator 102 includes linear polarizer 104, linear retarder 105 at azimuth 45°, and achromatic quarter-wave retarder 106 at azimuth 0°. The linear polarizer 104 can be oriented at angle β, as it is illustrated by arrow 107. The light propagation direction is depicted by arrow 108. The bandpath filter 103 selects required spectrum in the beam radiated by light source 101. Illumination and imaging beams are separated by non-polarizing beamsplitter 1401. Polychromatic polarization state generator 102 functions twice, as polarization state generator in the illumination beam and as polarization state detector in the imaging (reflected) beam. Objective lens 403 is also employed twice, for illuminating the specimen and for imaging purpose. If the linear polarizer 104 is orientated at angle β=0° then all spectral components of the illuminating beam are circularly polarized. Thus, the polarization state generator 102 works as achromatic circular polarizer. Because all spectral components change their handedness during reflection the polarization state generator blocks the reflected light. In this case the polarization state generator 102 works as achromatic circular analyzer. The low-birefringent specimen is seen colorless. Rotating the polarizer 104 (β≠0°) creates gray non-birefringent background and causes appearance of the birefringent colors. The shown reflected polscope schematic can also employ the second embodiment of polychromatic polarization state generator 201 (see FIG. 2A) instead of first embodiment of polychromatic polarization state detector 301.

Figure 17:
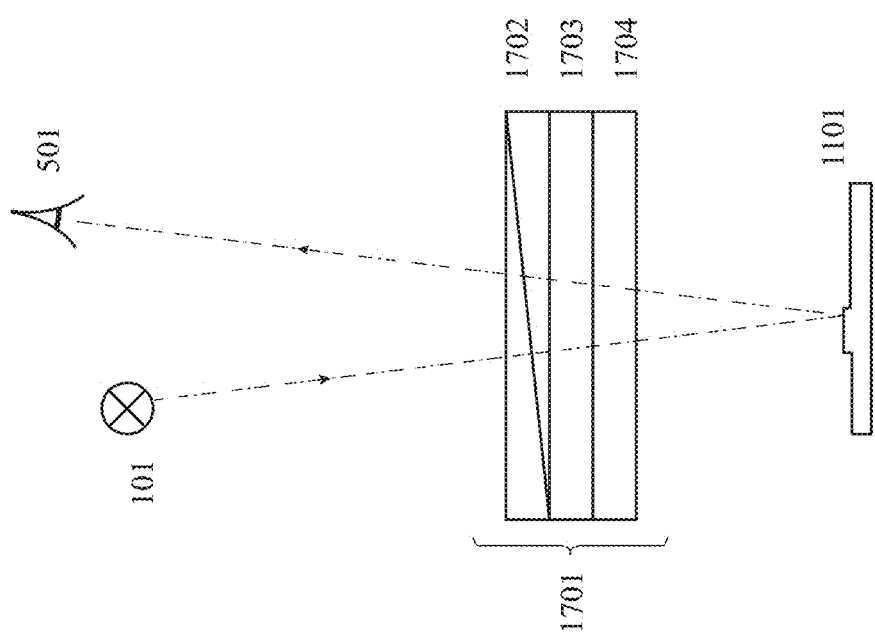
FIG. 17 is a schematic drawing of reflected polychromatic polscope for visual observation of birefringence with the first embodiment of polychromatic polarization state generator, which is built as a composite film.

FIG. 17 shows a schematic of reflected polychromatic polscope for visual observation of birefringence with the first embodiment of polychromatic polarization state generator, which is built as a composite film. This polscope consists of a light source 101, polychromatic polarization state generator 1701, and reflecting birefringent specimen under investigation 1101. This setup is a modification of polscope that is depicted in FIG. 16, where an eye 501 replaces the color CCD camera 302. The polychromatic polarization state generator 1701 is built with using polarizing film 1702, birefringent retardation film 1703 at azimuth 45°, and achromatic quarter-wave birefringent film 1704 at azimuth 0°. The polarizing film is oriented at selected predetermined angle β to achieve the best contrast for selected specimen retardance range. The birefringent retardation film 1703 has the same retardation as the linear retarder 105, and the achromatic quarter-wave birefringent film 1704 has the same retardation as achromatic quarter-wave retarder 106. Polychromatic polarization state generator 1701 functions twice, as polarization state generator in the illumination beam and as polarization state detector in the imaging (reflected) beam. The shown reflected polscope can also employ the second embodiment of polychromatic polarization state generator 201 (see FIG. 2A) instead of first embodiment of polychromatic polarization state generator 1701. Reflected polychromatic polscope, which is shown in FIG. 17, functions is the same way as reflected polscope depicted in in FIG. 16

Figure 18:
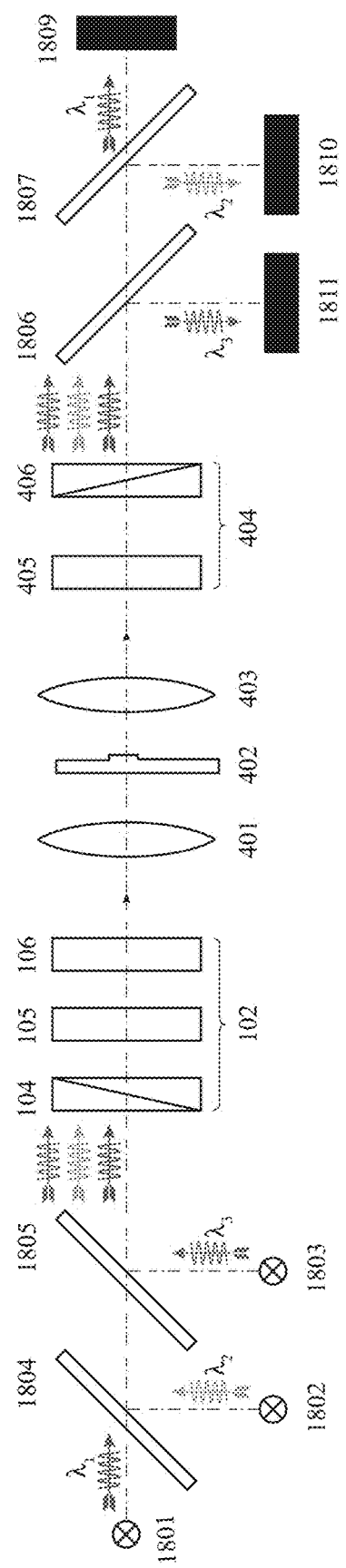
FIG. 18 is a schematic drawing of 3-wavelength transmitting polychromatic polscope for quantitative birefringence imaging.

FIG. 18 shows a schematic of 3-wavelength transmitting polychromatic polscope for quantitative birefringence imaging. The setup includes three monochromatic or narrow band light sources 1801, 1802, and 1803 with wavelengths $\lambda_1$, $\lambda_2$, and $\lambda_3$, respectively, four dichromatic mirrors 1804, 1805, 1806, and 1807, the first embodiment of polychromatic polarization state generator 102, condenser lens 401, birefringent specimen under investigation 402, objective lens 403, achromatic circular analyzer 404, and three monochromatic CCD cameras 1809, 1810, and 1811. The polychromatic polarization state generator 102 includes linear polarizer 104, linear retarder 105 at azimuth 45° and achromatic quarter-wave retarder 106 at azimuth 0°. The linear polarizer can be oriented at selected angle. The achromatic circular analyzer 404 could be formed by achromatic quarter waveplate 405 with orientation 45° and linear polarizer 406 with orientation 0°. The shown schematic can also employ the second embodiment of polychromatic polarization state generator 201 (see FIG. 2A) instead of first embodiment of polychromatic polarization state generator 102.

The polscope setup that is represented in FIG. 18 works in the following way. Dichromatic mirrors 1804 and 1805 combine three monochromatic or narrow band illumination beams, which are radiated by the light sources 1801, 1802, and 1803. The combined beam consisting of wavelengths $\lambda_1$, $\lambda_2$, and $\lambda_3$ passes through the polychromatic polarization state generator 102, which creates three polarization ellipses. The output polarization ellipses have different orientations, according to the wavelength. The elliptically polarized beam is focused by condenser 401 on the specimen 402. Objective lens 403 forms the imaging beam, which passes through achromatic circular analyzer 404. Then the combined beam is separated into three monochromatic or narrow band beams by dichromatic mirrors 1806, and 1807. The corresponding images are registered by three monochromatic CCD cameras 1809, 1810, and 1811. The obtained images are used for computing maps of retardance and slow azimuth distribution according to three-frame algorithm, which we proposed early (M. Shribak, "Complete polarization state generator with one variable retarder and its application for fast and sensitive measuring of two-dimensional birefringence distribution", The Journal of the Optical Society of America A, vol. 28, No. 3, 410-419 (2011)).

Figure 19:
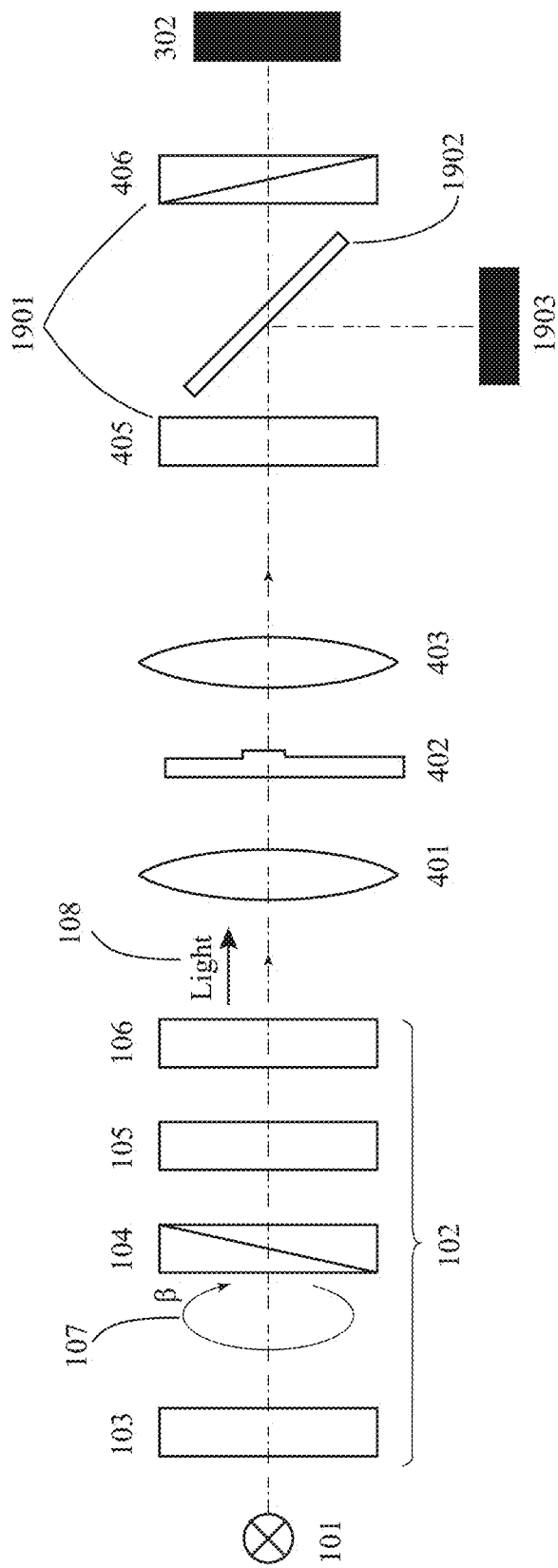
FIG. 19 is a schematic drawing of a transmitting polychromatic polscope with simultaneous polarization and brightfield imaging modalities.

FIG. 19 shows a schematic of transmitting polychromatic polscope with simultaneous polarization and brightfield imaging modalities. The polychromatic polscope consists of light source 101, first embodiment of polychromatic polarization state generator 102, condenser lens 401, birefringent specimen under investigation 402, objective lens 403, achromatic circular analyzer 1901, non-polarizing beamsplitter 1902, and color CCD cameras 302 and 1903. The polychromatic polarization state generator 102 includes bandpass filter 103, linear polarizer 104, linear retarder 105 at azimuth 45° and achromatic quarter-wave retarder 106 at azimuth 0°. The linear polarizer can be oriented at angle β, as it is shown by arrow 107. The light beam propagation direction is shown by arrow 108. The achromatic circular analyzer 1901 could be formed by achromatic quarter waveplate 405 with orientation 45° and linear polarizer 406 with orientation 0°. The shown schematic can also employ the second embodiment of polychromatic polarization state generator 201 (see FIG. 2A) instead of first embodiment of polychromatic polarization state generator 102.

The polscope setup that is represented in FIG. 19 works in the following way. Light beam, which is radiated by the light source 101, propagates through the polychromatic polarization state generator 102. The generator forms a set of polarization ellipses with certain spectral distribution of the major axis (see FIG. 1B or FIG. 2B). Then condenser 401 illuminates a selected area of the specimen 402. Birefringent structures of the specimen modify the beam polarization. Objective lens 403 creates the imaging beam, which is split by non-polarizing beamsplitter 1902. The non-polarizing beamsplitter 1902 is sandwiched between achromatic quarter waveplate 405 and linear polarizer 406. Because the beamsplitter incidence plane is parallel to the principal plane of the polarizer 406, the beamsplitter does not alter functionality of the achromatic circular analyzer 1901. Beam, which is transmitted by non-polarizing beamsplitter 1902, creates a color birefringent image on the color CCD camera 302. This microscope part functions in the same way as transmitted polscope depicted in FIG. 4. Beam, which is reflected by non-polarizing beamsplitter 1902, creates a conventional non-polarized brightfield image on the color CCD camera 1903.

Figure 20:
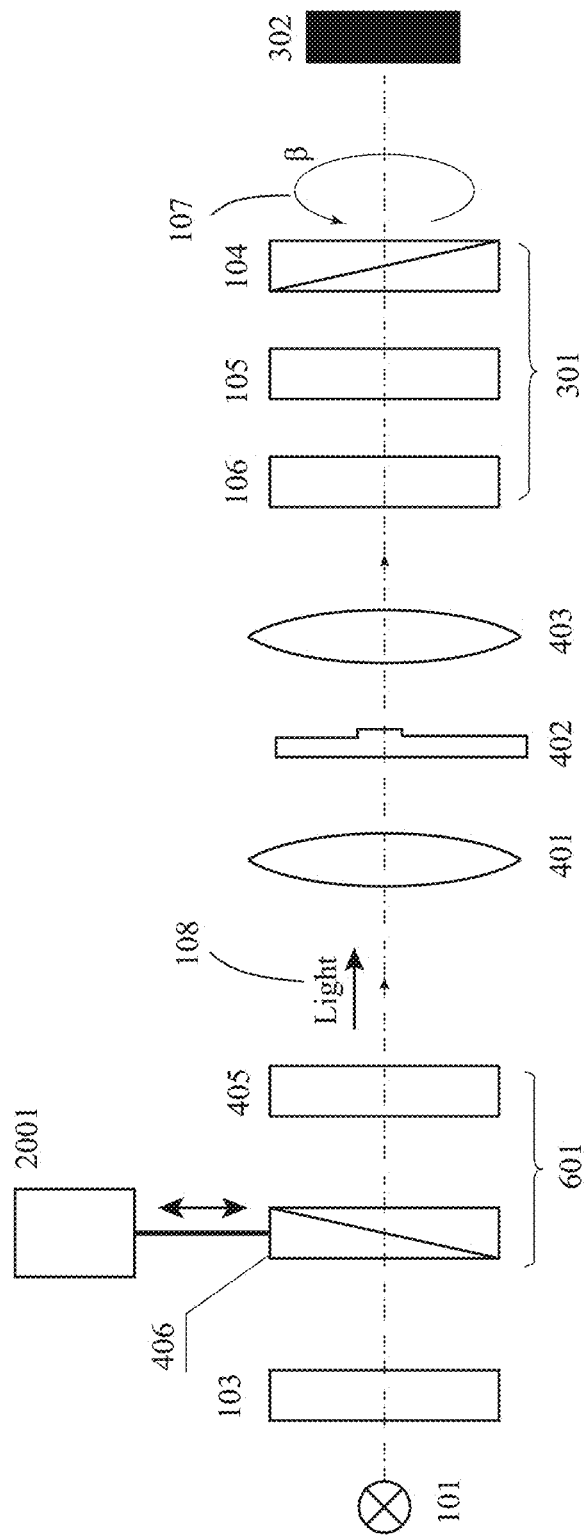
FIG. 20 is a schematic drawing of a transmitting polychromatic polscope with switched polarization and brightfield imaging modalities.

FIG. 20 shows a schematic of transmitting polychromatic polscope with switched polarization and brightfield imaging modalities. The polychromatic polscope consists of light source 101, bandpass filter 103, achromatic circular polarizer 601, condenser lens 401, birefringent specimen under investigation 402, objective lens 403, first embodiment of polychromatic polarization state detector 301, and color CCD camera 302. Linear polarizer 406 with orientation 0° and achromatic quarter waveplate 405 with orientation 45° form achromatic circular polarizer 601. Driver 2001 is mechanically connected to the linear polarizer 406 and can move the polarizer in and out of the optical path. The polychromatic polarization state detector 301 includes achromatic quarter-wave retarder 106, linear retarder 105 and linear polarizer 104. The linear polarizer 104 can be oriented at angle β, as it is illustrated by arrow 107. The light beam propagation direction is depicted by arrow 108. The shown schematic can also employ the second embodiment of polychromatic polarization state generator 201 (see FIG. 2A) in the inverse orientation instead of first embodiment of polychromatic polarization state detector 301.

The polscope setup that is represented in FIG. 20 works in the following way. If the linear polarizer 406 is positioned in the optical path then the setup functions in the same way as transmitted polscope depicted in FIG. 6 and color camera 302 captures color birefringent image. If the linear polarizer 406 is taken out from the optical path then the color camera 302 captures conventional non-polarized brightfield image. Similar switch between polarization and brightfield imaging modalities can be achieved by moving the linear polarizer 104 from the optical path. However moving the linear polarizer 406 is preferable because it does not introduce displacement of the image.

Diatom *Arachnoidiscus* is an excellent specimen for demonstrating advantages of the polychromatic polscope. It has silicified cell wall, which forms a radially symmetric pillbox-like shell (frustule) composed of overlapping halves that contain intricate and delicate patterns. Sometime it is called "a wheel of glass". Diatom *Arachnoidiscus* deserves the term of "living photonic crystals" and was employed for enabling sub-diffractive focusing with better confining of the light beam than other far-field super focusing approaches. Birefringence of the *Arachnoidiscus* structure is very low, except the central radial filaments that exhibit slightly elevated retardance. According to our measurement, retardance of the central filaments is about 5 nm.

Figure 21:
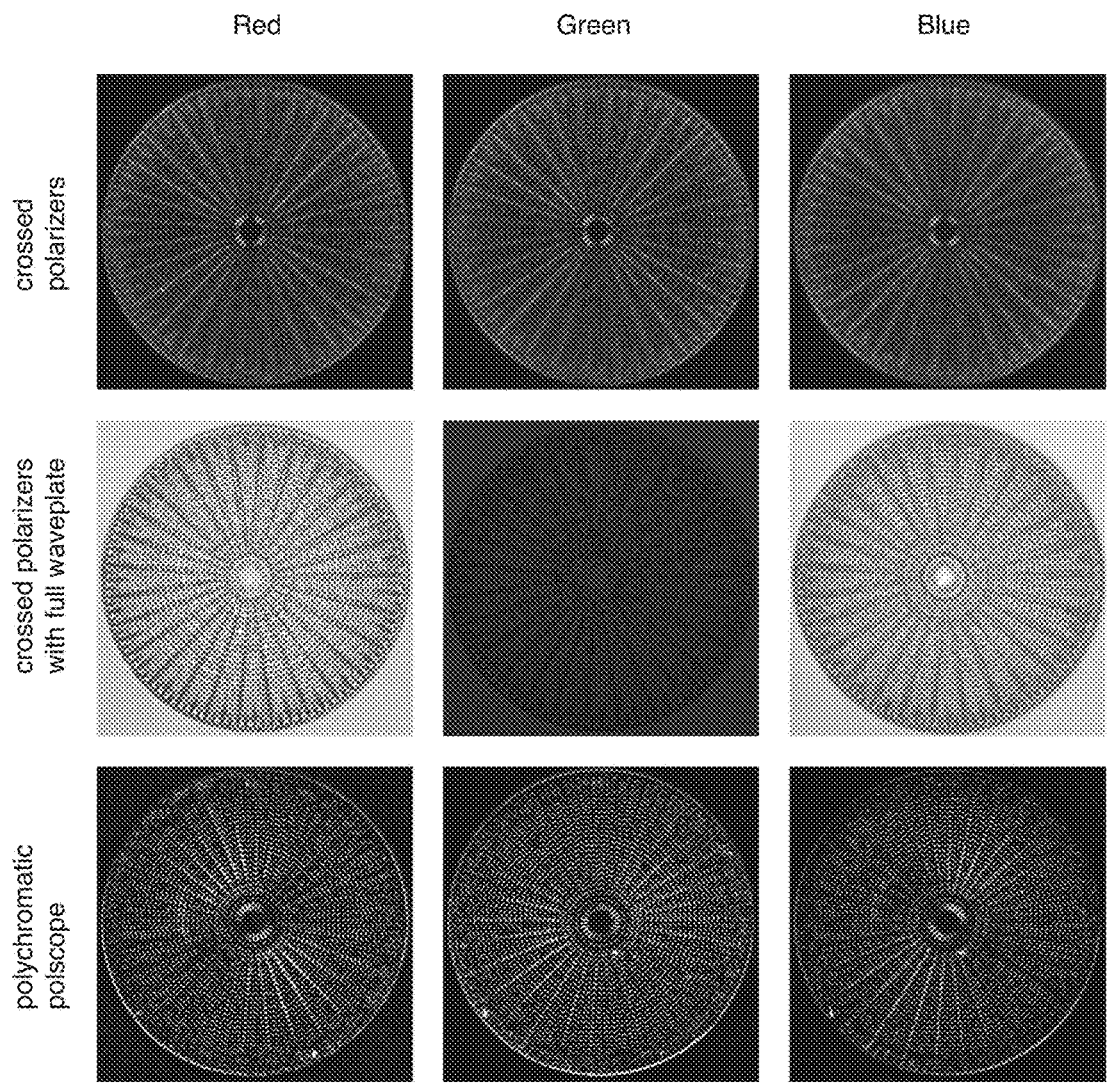
FIG. 21 shows three sets of RGB images of a diatom *Arachnoidiscus* captured with two regular polarized light microscopes and polychromatic polscope.

Three color images of the diatom *Arachnoidiscus*, which were taken with various polarized light techniques, are shown in FIG. 21. Diatom *Arachnoidiscus Ehrenbergi* microscope slide (Turtox slide series No. B1.144 "Diatoms") was manufactured by General Biological Supply House, Inc. (Chicago, Ill., USA). We used an upright light microscope Olympus BX61 (Olympus America, Center Valley, Pa., USA) equipped with objective lens UPlanFl 40x/0.75P and 100 W halogen lamp U-LH100-3-5. All images were taken in white light without any filter. The images were captured with consumer SLR camera Nikon D40x (Nikon, Melville, N.Y., USA). The image size is 190 μm×190 μm. The color images in FIG. 21 are represented as grayscale pictures in the red, green and blue color channels (left, central and right columns, respectively).

The top row depicts a case with crossed linear polarizer and analyzer. The red, green and blue pictures are practically the same because the original color image is grey. The central radial filaments are slightly brighter at the diagonal directions. Vertical and horizontal filaments are dark. The brightness depends on the filament orientation.

We can also shift the Newton colors by adding a full-wave plate (retardance ~550 nm), which is also known as "sensitive" or "red" waveplate. The middle row illustrates a case with crossed linear polarizer and analyzer plus a full-wave plate, which is inserted into the optical path. We employed a first order red, full-wave plate Olympus U-TP530. The entire image is purple with a hardly visible hue change in the central diagonal filaments.

The bottom row shows a RGB decomposition of color image taken with polychromatic polscope. It shows the diatom image after background subtraction. The brightness corresponds to retardance and hue represents the slow axis orientation. The filaments, which is oriented in 5-11 direction is brightest in the red image and dimmest in the blue image. The filaments, which are oriented in 3-9 (horizontal) direction, are brightest in the green image and dimmest in the red and blue images. The filaments, which is oriented in 1-7 direction is brightest in the blue image and dimmest in the red image. The colors confirm that birefringent structure of diatom has radially oriented principal axes.

Thus while specific embodiments have been shown, it is understood that alternatives and equivalent constructions are possible, and that the invention can be used together with a variety of imaging systems, and in combination with image processing and data analysis techniques, as will be known by those skilled in these arts. Moreover, while there have shown and described and pointed out fundamental novel features of the invention as applied to preferred embodiments thereof, it will be understood that various omissions and substitutions and changes in the form and details of the methods described and devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. In addition, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. An apparatus for imaging birefringence in a sample, comprising:
    an illuminator for providing an illumination light;
    optics for directing the illumination light toward the sample;
    a detector for registering color images;
    optics for directing light that has interacted with the sample toward the detector;
    two polarization state generators;
    wherein:
        one polarization state generator is located between the illuminator and the sample; and
        another polarization state generator is located between the sample and the detector; and
        at least one of the polarization state generators is the polychromatic polarization state generator for selectively transmitting light that has a selected elliptical polarization state with selected ellipticity and the major axis orientation of the polarization ellipses, which is a one-to-one function of wavelength in the selected spectral domain.

2. The apparatus of claim 1, wherein the illumination light is transmitted by the sample.

3. The apparatus of claim 1, wherein the illumination light is reflected by the sample.

4. The apparatus of claim 1, wherein said two polarization state generators are polychromatic polarization state generators.

5. The apparatus of claim 4, wherein said two polychromatic polarization state generators have substantially mutually orthogonal polarizations states.

6. The apparatus of claim 4, wherein said two polychromatic polarization state generators have substantially same polarizations states.

7. The apparatus of claim 1, wherein one of said polarization state generators is an achromatic circular polarizer for selectively transmitting light that is substantially circularly polarized in for about all used wavelengths.

8. The apparatus of claim 7, wherein:
    the polychromatic polarization state generator is located between the illuminator and the sample; and
    the achromatic circular polarizer is located between the sample and the detector.

9. The apparatus of claim 7, wherein:
    the achromatic circular polarizer is located between the illuminator and the sample; and
    the polychromatic polarization state generator is located between the sample and the detector.

10. The apparatus of claim 1, wherein the polychromatic polarization state generator comprising:
    an optical system for selectively transmitting light with selected spectrum;
    a polarizer for selectively transmitting light that has a selected polarization state;
    a polarization converter for transforming the initial selected polarization state into a set of output polarization states with polarization ellipses, which have selected ellipticity, and a dependence of the major axis orientation of the polarization ellipses on the wavelength is a one-to-one function in the selected spectral domain.

11. The polychromatic polarization state generator of claim 10, wherein said selected spectrum is selected continuous spectrum.

12. The polychromatic polarization state generator of claim 11, wherein said selected spectrum is visible spectrum from about 400 nm to about 700 nm.

13. The polychromatic polarization state generator of claim 10, wherein said selected spectrum comprises of two or more selected discrete wavelengths.

14. The polychromatic polarization state generator of claim 10, wherein said polarizer is rotatable linear polarizer and said polarization converter consists of sequence of linear retarder and achromatic quarter-wave retarder; wherein:
    the phase difference of said linear retarder is approximately inversely proportional to the wavelength; and
    the principal axes of said linear retarder and said achromatic quarter-wave retarder create angle about 45° or about −45°.

15. The polychromatic polarization state generator as claimed in claim 14, wherein the phase difference of said linear retarder at the shortest wavelength is approximately equal to the phase difference at the longest wavelengths plus about 360 degrees.

16. The polychromatic polarization state generator of claim 10, wherein said polarizer is a rotatable linear polarizer and said polarization converter consists of sequence of an achromatic quarter-wave retarder and polarization rotator, wherein the polarization rotation angle of said polarizer rotator is approximately inversely proportional to the wavelength.

17. The polychromatic polarization state generator of claim 16, wherein the polarization rotation angle of said polarization rotator at the shortest wavelength is approximately equal to its polarization rotation angle at the longest wavelengths plus about 180 degrees.

18. The polychromatic polarization state generator of claim 16, wherein said polarization rotator is a plane parallel plate, which is cut from crystal quartz about perpendicular to the optical axis (z-cut).

* * * * *